United States Patent [19]

Oiry et al.

[11] Patent Number: 4,816,482

[45] Date of Patent: Mar. 28, 1989

[54] RADIOPROTECTIVE AGENTS HAVING AN AMINO-THIOALKYL STRUCTURE

[75] Inventors: Joël Oiry; Jean-Louis Imbach, both of Montpellier, France

[73] Assignee: Centre National de la Recherche Scientifique (CNRS), Paris, France

[21] Appl. No.: 704,548

[22] Filed: Feb. 22, 1985

Related U.S. Application Data

[63] Continuation of PCT FR84/00159, Jun. 20, 1984, published as WO85/00167 on Jan. 17, 1985.

[30] Foreign Application Priority Data

Jun. 22, 1983 [FR] France ................................ 83 10318

[51] Int. Cl.$^4$ ................... C07C 153/04; A61K 31/265
[52] U.S. Cl. ....................................... 514/513; 558/254
[58] Field of Search ......................... 558/254; 514/513

[56] References Cited

U.S. PATENT DOCUMENTS 2,574,996 11/1951 Allen et al. .......................... 558/254

Primary Examiner—Alan L. Rotman
Assistant Examiner—Robert C. Whittenbaugh
Attorney, Agent, or Firm—Wegner & Bretschneider

[57] ABSTRACT

A pharmaceutical composition effective in the protection of normal tissues against radiation induced damage comprising administration a compound of the formula $$R_1-CO-NR_3-/A/-S-R_2$$

in which $R_1$ is a radical corresponding to an amino acid $R_1$—COOH, /A/ is a $C_2$ or $C_3$ alkylene radical which can be substituted with a $C_1$ to $C_3$ alkyl radical, or with a hydroxy or hydroxycarbonyl radical or a —COR radical where R is an amino or —NH—$CH_2$—$CO_2H$ radical, $R_2$ is an acyl radical which protects the thiol group and which liberates the thiol group in vivo, $R_3$ is a hydrogen, and also the salts of this compound with pharmaceutically acceptable acids.

10 Claims, No Drawings

RADIOPROTECTIVE AGENTS HAVING AN AMINO-THIOALKYL STRUCTURE

This application is a continuation of International Application PCT/FR84/00159 filed June 20, 1984 published as WO85/00167 on Jan. 17, 1985.

Radioprotectors represent a class of compounds which has been a subject of special study in the literature, and they are for the most part characterised by the presence of an SH group or one of its bio-precursors. (sic).

The chief mode of action of these compounds is linked to the capacity possessed by the thiol group for trapping free radicals induced intracellularly to radiations of various natures, thereby preventing permanent damage to the cells.

A typical structure, among those most extensively studied, is that of cysteamine (or MEA) (1):

$$NH_2-CH_2-CH_2-SH \qquad (1)$$

and currently the most active radioprotector is a cysteamine derivative of structure (2): WR 2721

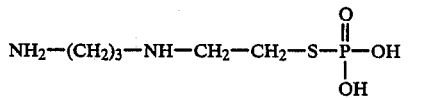

$$NH_2-(CH_2)_3-NH-CH_2-CH_2-S-\overset{\overset{O}{\|}}{\underset{\underset{OH}{|}}{P}}-OH \qquad (2)$$

This compound is substituted on the N-terminal side of the cysteamine by an aminoalkyl chain, and on the S-terminal side by a phosphorothioate group which possesses the two-fold advantage of endowing the molecule with high solubility in water and, in an initial stage, of protecting the thiol group which can be liberated "in situ" by the action of phosphatases or even by hydrolysis.

In general, radioprotectors lead to a non-selective protection of the cells, regardless of whether they are healthy or malignant (for example cysteamine, cysteine, and the like).

However, WR 2721 possesses the exceptional property of selectivity protecting normal tissues against radiation-induced damage, while allowing solid tumors to bear alone the effect of the radiation.

In other words, this drug concentrates selectively in healthy cells and not in cancer cells. The origin of this selectivity is not yet soundly established.

Nevertheless, the value of this new class of selective radioprotectors is very significant by virtue of their potential use in radiotherapy, which would enable the number of induced cancers to be reduced.

It would also appear that WR 2721 may exert a selective protective effect during chemotherapy with alkylating drugs such as cis-platinum, cyclophosphamide and nitrogen mustards. Furthermore, this compound is the first radioprotector approved by the FDA, and it has been the subject of phase I studies in both the United States of America and Japan.

The present invention relates to cysteamine derivatives which possess good selective radioprotective ability and some of which are inducers of interferon.

The compounds according to the present invention correspond to the formula:

$$R_1-CO-Y-/A/-Y'-R_2$$

in which one of Y and Y' denotes —S—, and the other denotes —NR$_3$—.

More especially, the compounds according to the present invention correspond to the formula Ia or Ib:

$$R_1-CO-NR_3-/A/-S-R_2 \qquad (Ia)$$

$$R_1-CO-S-/A/-NR_3-R_2 \qquad (Ib)$$

in which $R_1$ is a radical corresponding to an amino acid or a di- or tripseudopeptide $R_1$—COOH, /A/ is a $C_2$ or $C_3$ alkylene radical which can be substituted with one or more $C_1$ to $C_3$ alkyl radicals, a free or esterified hydroxy radical, a free or esterified hydroxycarbonyl radical or a —COR radical in which R is an amino or —NH—CH$_2$—CO$_2$—H radical, $R_2$ is a radical which protects the thiol group and which liberates the thiol group "in vivo", $R_3$ is hydrogen or a $C_1$ to $C_3$ alkylene radical or, when joined to the group $R_2$, forms a ring which protects the thiol group.

The invention also relates to the salts of these compound with pharmaceutically acceptable acids.

Among amino acids of formula $R_1$—COOH, there should be mentioned those in which $R_1$ is a linear or branched $C_1$ to $C_7$ alkylamino radical, especially a $C_1$ to $C_4$ alkylamino radical, such as derivatives of alanine, glycine and sarcosine, as well as alkyl derivatives substituted on the amine. The radical $R_1$ can also originate from a di- or tripseudopeptide, "pseudopeptide" being understood to denote a linkage of 2 or 3 amino acids, natural or otherwise, such as those defined above, for example a gly-gly or ala-gly linkage.

$R_2$ is defined as a radical which protects the thiol group, and this is true in the correct sense in the case of the compounds (Ia), but for the compounds (Ib) which are symmetrical derivatives of (Ia), the definition is, in this case, functional, since $R_2$ is not on a sulphur atom but on an amino group, yet trials have shown that the two types of compounds (Ia) and (Ib) possess related properties.

Among the radicals $R_2$, various types of radicals can be envisaged depending on the nature of the reaction through which the thiol group will be liberated: either by S→N rearrangement, for example:

$$R_1-CO-NH-CH_2-CH_2-S-CR_5 8=R_4) \rightarrow$$
$$R_1-CO-N(R_4R_5)-CH_2-CH_2-S-H$$

where $R_4$=O, S, NH, N—(C$_1$-C$_7$)alkyl, $R_5$=H, C$_1$-C$_7$ alkyl, substituted or unsubstituted aryl, NH$_2$, SH; or by bioreductive activation of a disulphide bride, for example:

$$R_1-CO-NH-CH_2-CH_2-S \longrightarrow$$
$$\qquad\qquad\qquad\qquad\qquad | $$
$$\qquad\qquad\qquad\qquad\qquad R_6-S$$

$$R_1-CO-NH-CH_2-CH_2-SH + R_6SH$$

where
$R_6$ can be an $R_7$—CO—NR$_3$—/A/ chain, that is to say the compound can be a cystamine derivative, or alternatively an unsubstituted or substituted aryl or C$_1$-C$_7$alkyl radical;
or by enzymatic or non-enzymatic hydrolysis, in which case $R_2$=SO$_3$H or PO$_3$H$_2$ or a C$_2$ to C$_7$ alkanyloxy (sic) group;

finally, the thiol group can be masked by inclusion in a cyclic structure of the thiazole type, namely:

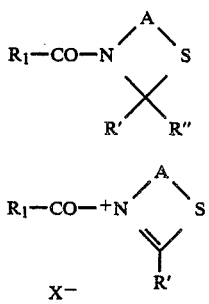

where R'=H, $C_1$-$C_7$alkyl, aryl, $NH_2$, R"=H, $C_1$-$C_7$alkyl, aryl.

Most of these compounds which possess basic nitrogen atoms can be prepared in the form of quaternary salts. The anion $X^-$ used being diverse in nature, for example: $Br^-$, $Cl^-$, $CF_3CO_2^-$, $CH_3$—$C_6H_4$—$SO_3^-$, $CH_3CO_2^-$.

Among the aryl radicals referred to, there should be mentioned monocyclic aryl radicals, in particular the phenyl radical which can be substituted with one or more halogen atoms, in particular chlorine, or with one or more $C_1$-$C_3$alkyl or hydroxy radicals.

Among the preferred compounds of the present invention, there should be mentioned the compounds of formula:

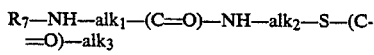

and

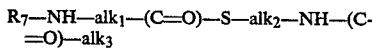

in which $R_7$ is H or a $C_1$ to $C_3$ alkyl radical, $alk_1$ is a linear or branched $C_1$ to $C_7$ alkylene chain, $alk_2$ is an ethylenyl or propylenyl chain bearing one or more free or esterified methyl or hydroxy radicals, $alk_3$ is a $C_1$-$C_7$alkyl radical either unsubstituted or substituted with one or more chlorine atoms, and in particular: N-glycyl-S-acetylcysteamine,
N-L-alanyl-S-acetylcysteamine,
N-γ-aminobutyryl-S-acetylcysteamine,
N-glycyl-S-(dichloroacetyl)cysteamine,
2-glycylamino-2,2-dimethyl-1-(thioacetyl)ethane I 108,
3-glyclamino-2-acetoxy-1-(thioacetyl)propane I 111,
glycyl-[2-methyl-2-(acetylmercapto)ethyl]amine I 118,
N-sarcosyl-S-acetylcysteamine I 123,
2-glycylthio-1,1-dimethyl-1-acetamidoethane I 107,
S-glycyl-N-acetylcysteamine I 114,
and also the corresponding quaternary ammonium salts, and also the compounds of formula:

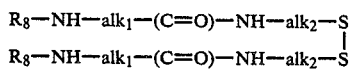

in which $R_8$ is H or a $C_1$ to $C_3$ alkyl radical, $alk_1$ is a linear or branched $C_1$ to $C_7$ alkylenyl chain and $alk_2$ is an ethylenyl or propylenyl chain bearing one or more free or esterified methyl or hydroxy radicals, and in particular:
N,N'-diglycylcystamine,
N,N'-di-L-alanylcystamine,
N,N'-di-(γ-aminobutyryl)cystamine,
1,2-di-(3-glycylamino-2-acetoxypropyl) disulphide I 110,
N,N'-disarcosylcystamine I 124,
and also the corresponding quaternary ammonium salts.

The compounds of the above formulae are also useful when $R_7$ or $R_8$ denotes the radical of an amino acid or a dipeptide, especially when $R_7$ or $R_8$ denotes

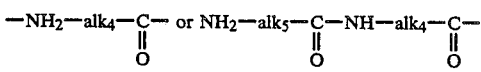

for example, $alk_4$ and $alk_5$ being linear or branched $C_1$ to $C_7$ alkylene radicals, preferably $C_1$ to $C_4$ radicals.

Among these compounds, there should be mentioned: N,N'-di-(glycylglycyl)cystamine I 116, N-glycylglycyl-S-acetylcysteamine I 109.

Among other useful compounds, there may be mentioned the compounds of formula:

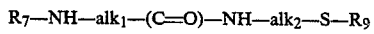

in which $R_7$, $alk_1$ and $alk_2$ have the significance given above and $R_9$ is

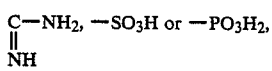

or salts of these groups.

There may be mentioned in particular: glycyl-(2-isothiouronioethyl)amine, 2-(glycylamino)ethylthiosulphuric acid, sodium S-(2-glycylaminoethyl)phosphorothioate.

One of the advantages of the compounds according to the invention, relative to the product WR 2721, is that they are more stable.

The compounds according to the present invention can be prepared by processes similar to those used in peptide synthesis.

The significances of the abbreviations used have been collated at the end of the description.

The compounds according to the invention are generally obtained by deprotection of a compound of formula:

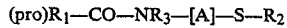

eliminating the (pro) group or groups which protect the amino radical, the protective groups preferably being benzyloxycarbonyl and tert-butoxycarbonyl groups. The protective compounds can be synthesised as described below.

Thus, the compounds are obtained by coupling an AA having its N protected by Z or BOC with an S-substituted cysteamine (β-mercaptoethylamine, MEA) (Scheme 1). The condensation solvents are ethyl acetate or THF. DCC or t-PNC (J. Martinez et al., Bull. Soc. Chim. Fr., 1972, 12, 4707) in the presence of TEA are the coupling agents.

The terminal amino groups are then deprotected, either by hydrobromic acid in glacial acetic acid solution at low temperature for Z groups or by trifluoroacetic acid for BOC groups, and are obtained in the form of hydrobromides or trifluoroacetates.

Replacement of the amino acid by a dipeptide or tripeptide enables the same S-substituted derivatives as in Scheme 1 to be obtained for pseudo-dipeptide or tripeptide series, and the like. Likewise, extension of the chain on the N-terminal side can be accomplished by further coupling with another amino acid or with a dipeptide, or the like, which is correctly protected or activated.

-continued
SCHEME 1

S—substituted Z or BCC ... A'A'—AA—MEA

↓

S—substituted HBr or TFA, ... A'A'—AA—MEA

SCHEME 2

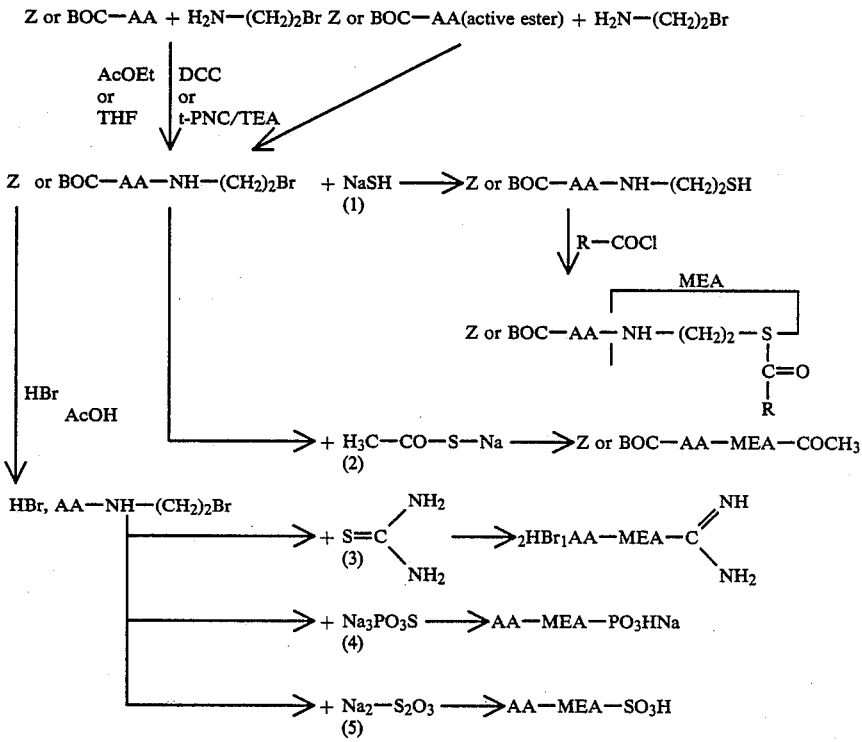

It is also possible to repeat all the above stages but using a haloalkylamine instead of S-substituted MEA. The halogenated pseudopeptides, especially brominated pseudopeptides, will then be condensed with suitable reagents to obtain the same compounds (Scheme 2).

SCHEME 1

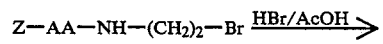

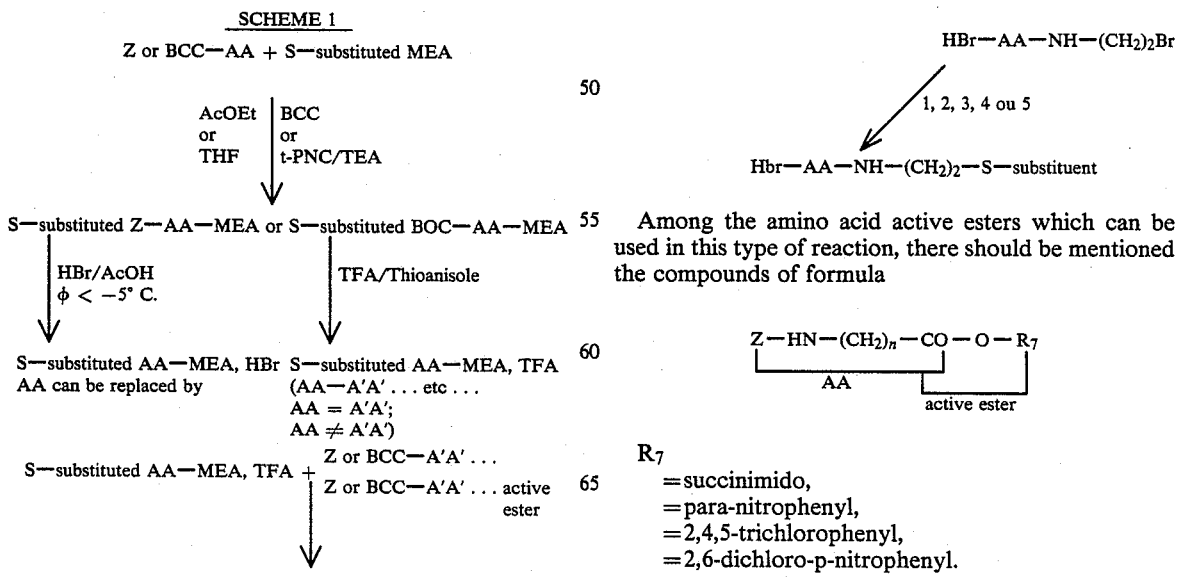

It is also possible to arrive at the same S-substitutions in the following manner:

Z—AA—NH—(CH$_2$)$_2$—Br $\xrightarrow{\text{HBr/AcOH}}$

HBr—AA—NH—(CH$_2$)$_2$Br

↓ 1, 2, 3, 4 ou 5

Hbr—AA—NH—(CH$_2$)$_2$—S—substituent

Among the amino acid active esters which can be used in this type of reaction, there should be mentioned the compounds of formula Z—HN—(CH$_2$)$_n$—CO—O—R$_7$
         AA
              active ester R$_7$
= succinimido,
= para-nitrophenyl,
= 2,4,5-trichlorophenyl,
= 2,6-dichloro-p-nitrophenyl.

The synthesis of the cystamine derivatives can be carried out according to two different methods:

Method using the above MEA derivatives (Scheme 3)

The two S-substituted pseudopeptides having their N protected by Z or BOC are hydrolysed on the S-terminal side by sodium methylate, and then oxidised by iodine in aqueous acetic acid to form the di-Z or di-BOC cystamine pseudopeptides. The terminal amino groups are then deprotected by hybrobromic acid in glacial acetic acid solution or by trifluoroacetic acid in the presence of thioanisole. The pseudopeptides are obtained in the form of their dihydrobromides or di(trifluoroacetates).

It is also possible to avoid a stage by using a halogenated derivative (Z or BOC) which will be condensed with sodium hydrosulphide and form the corresponding Z-AA-MEA or BOC-AA-MEA thiol directly.

Method using cystamine (Scheme 4)

In this case, di-Z-AA-cystamine or di-BOC-AA-cystamine is obtained directly. These derivatives are synthesised by condensation, in DMF in the presence of TEA, of a Z-AA or BOC-AA, activated on the acid terminal side by a suitable ester, with cystamine.

The di-Z- or di-BOC-AA-cystamine are (sic) then treated with hydrobromic acid in glacial acetic acid solution or with trifluoroacetic acid to give their respective amine salts.

Di-Z- or di-BOC-AA-cystamine are also obtained from Z- or BOC-glycines and cystamine, using a coupling agent(t-PNC or DCC).

The amine salts can be released and replaced by other ions. Likewise, release of the salts of di(amino acid)-cystamines enables the chain to be increased on the N-terminal side with other amino acids, and tetra-pseudopeptides, and the like, to be formed by conventional coupling. It is also possible to obtain them by the conventional methods already mentioned, by coupling Z- or BOC- di-, tripeptides, and the like, unactivated or activated by an ester, with cystamine (Scheme 5).

SCHEME 4

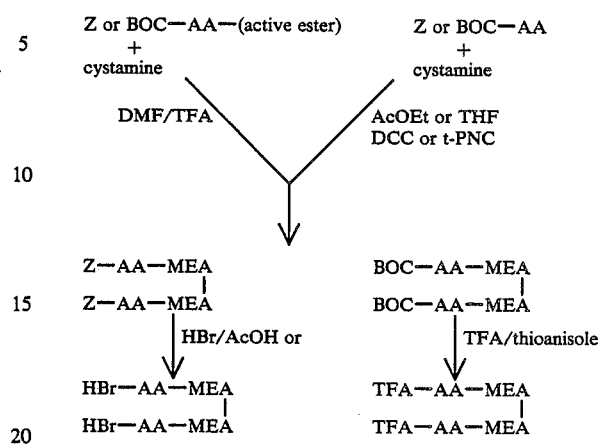

SCHEME 5

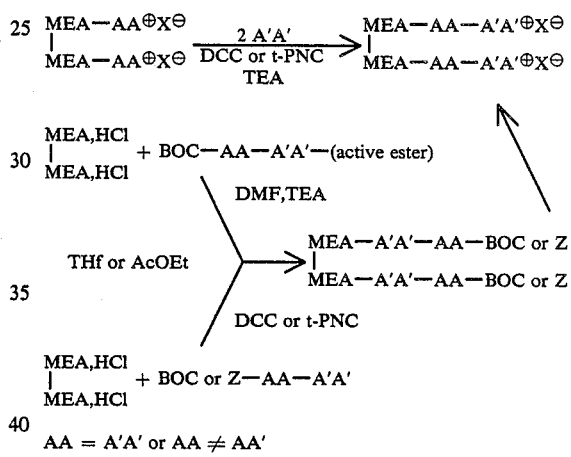

The present invention also relates to the application of the compounds according to the present invention by way of radioprotective agent, and pharmaceutical compositions containing them, for this type of application or

SCHEME 3

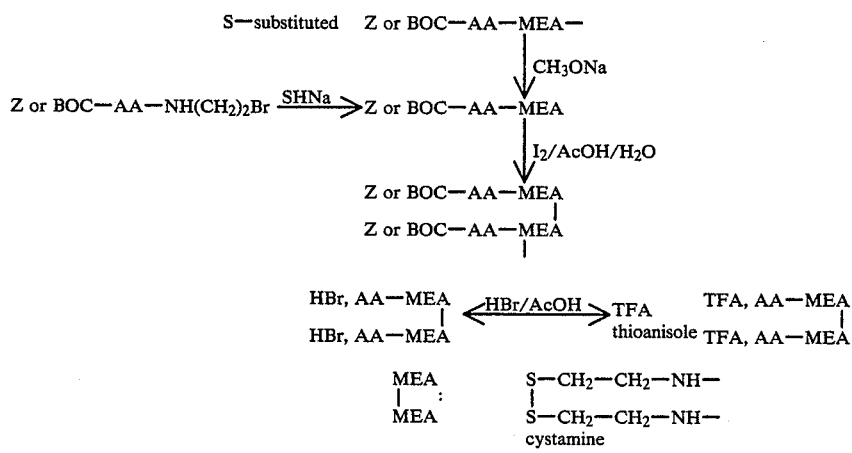

alternatively as an agent for inducing interferon in the treatment of diseases sensitive to interferon.

Other characteristics and advantages of the present invention will emerge on reading the examples below.

EXAMPLE 1

N-(Z-GLYCYL)-S-ACETYLCYSTEAMINE

General method of coupling involving a Z-AA

A solution of 4.598 g (0.022 mol) of Z-glycine in 80 ml of THF is stirred at 0° C. with 3.88 g (0.011 mole) of t-PNC [dichlohexylcarbodiimide (sic), DCC, also used, leads to the same yield] previously dissolved in 20 ml of THF or ethyl acetate. After 30 minutes' stirring at 0° C., 2.4 ml of TEA are added and the mixture is again left stirring for 30 minutes. After this time, a solution of 3.421 g (0.022 mole) of S-acetylcysteamine hydrochloride (prepared according to T. Wieland and E. Bokelmann, Ann. Chem., 1952, 576, 20) in 50 ml of THF or ethyl acetate is poured in. Stirring is maintained at 0° C. for 30 minutes, and the mixture is then allowed to return to room temperature, the basic pH being maintained by addition of TEA. The reaction is followed by TLC in a chloroform/methanol (9:1) eluent, and the time needed for coupling is approximately 2-3 hours in this case.

The mixture is then evaporated to dryness under reduced pressure and then taken up in 500 ml of ethyl acetate and 2×200 ml of ice-cold saturated aqueous sodium bicarbonate. The organic phase is then decanted and washed with 2×200 ml of ice-cold 5% strength aqueous hydrochloric acid and 2×200 ml of water (neutral pH), then dried over sodium sulphate and evaporated to dryness under vacuum. 5 g of a pale yellow oil are collected.

The product is purified by chromatography on a silica gel column (eluent: ethyl acetate/petroleum ether, 8:2).

TLC (chloroform/methanol, 9:1) $R_f$=0.5. Detection: UV or iodine vapour, Yld.=45%. Crystallises from ethyl acetate. M.p. 100°-103° C.

Analysis: $C_{14}H_{18}N_2SO_4$ (310): calculated %: C, 54.19; H, 5.80; N, 9.03; found %: C, 54.28; H, 5.68; N, 9.10.

IR spectrum (KBr) $vcm^{-1}$: 3320, 3280 (NH); 1665, 1625 (C=O); 1515 (amide I)

NMR spectrum (DMSO $d_6$): δ ppm: 7.33 (s-5H) benzyl; 6.75 and 5.75 (2m—2H)2NH (exchangeable with heavy water); 5.10 (s-2H) benzyl $CH_2$; 3.82 (d-2H) $CH_2CO$; multiplet between 2.70 and 3.60 (4H)$CH_2$—$CH_2$; 2.30 (s-3H) $COCH_3$.

EXAMPLE 2

N-GLYCYL-S-ACETYLCYSTEAMINE HYDROBROMIDE CL General method for unblocking the amine with formation of hydrobromide A mixture of 1.49 g (4.8×10$^{-3}$ mole) of N-(Z-glycyl)-S-acetylcysteamine and 4 ml of a freshly prepared solution of glacial acetic acid (ACOH) saturated with hydrobromic acid (HBr) is stirred at a temperature below −5° C. under an atmosphere of nitrogen, protecting the mixture from the light. The reaction is finished in 30 minutes. The hydrobromide is precipitated from the mixture by adding 80 ml of ice-cold anhydrous ether, and the ether phase is then decanted. This procedure of washing with ether is performed five times. The residual oil is then taken up in 30 ml of distilled water and lyophilised. The expected derivative is collected in a 90% yield in the form of a colourless, very hygroscopic paste. It will be stored under an atmosphere of nitrogen or under vacuum.

NMR spectrum (D$_2$O): 3.78 (s-2H) glycine $CH_2$; 3.46 (m-2H) N—$CH_2$; 3.05 (m-2H) S—$CH_2$; 2.35 (s-3H) $COCH_3$.

EXAMPLE 3

N-(Z-L-ALANYL)-S-ACETYLCYSTEAMINE

Coupling reaction according to the general method

Reagents used: 11.25 g (0.005 mole) of Z-alanine in 200 ml of THF. 8.7 g of t-PNC in 20 ml of THF. 7 ml of TEA. 7.75 g (0.005 mole of S-acetylcysteamine hydrochloride in 150 ml of THF.

The mixture is maintained basic by adding 7 ml of TEA and the reaction, followed by TLC (eluent: dichloromethane/methanol, 9:1), is finished in 4 hours. After the treatments already described, 15 g of an oil are obtained and this is chromatographed on a silica gel column (eluent: ethyl acetate/petroleum ether, 8:2). The expected derivative is collected in the form of an oil which crystallises in an ethyl acetate/petroleum ether (6:3) mixture. Yld.=80%. M.p. 78°-80° C.

Analysis: $C_{15}H_{20}N_2SO_4$ (324) calculated %: C, 55.55; H, 6.17; N, 8.64; found %: C, 55.72; H, 6.37; N, 8.67.

IR spectrum (KBr) $vcm^{-1}$: 3320, 3280 (NH): 1662, 1620 (C=O); 1520 (amide I).

NMR spectrum (CDCl$_3$) δppm: 7.36 (S-5H) benzyl; 7.0 (m-1 H, exchangeable with heavy water) NH—$CH_2$; 5.90 (d-1 H, exchangeable with heavy water) NH—CH; 5.11 (S-2H) benzyl $CH_2$; 4.23 (m-1H)—CH; 3.40 (m-2H) NH—$CH_2$; 3.0 (m-2H) S—$CH_2$; 2.30 (S-3H) CO—$CH_3$; 1.36 (d-3H) CH—$CH_3$.

EXAMPLE 4

N-L-ALANYL-S-ACETYLCYSTEAMINE HYDROBROMIDE

Preparation according to the general method described above

Reagents used: 1.418 g (4.3×10$^{-3}$ mole) of N-(Z-alanyl)-S-acetylcysteamine. 3 ml of HBr/AcOH.

After lyophilisation in 8 ml of water, 1.19 g of hydrobromide (hygroscopic) is collected.

NMR spectrum (D$_2$O) δppm: 4.10 (m-1H) CH; 3.50 (m-2H) N—$CH_2$; 3.10 (m-2H) S—$CH_2$; 2.38 (S-3H) $COCH_3$; 1.50 (d-3H) CH—$CH_3$.

EXAMPLE 5

N-(Z-γ-AMINOBUTYRYL)-S-ACETYLCYSTEAMINE

Coupling reaction according to the general method

Reagents used: 9.48 g (0.04 mole) of Z-γ-aminobutyric acid (prepared according to R. L. Evans et at., J. Org. Chem., 1959, 24, 863-4) in 75 ml of ethyl acetate. 7.95 g (0.02 mole) of t-PNC in 18 ml of ethyl acetate. 8 ml of TEA. 6.22 g (0.04 mole) of S-acetylcysteamine hydrochloride in 50 ml of ethyl acetate.

The mixture is maintained basic by adding 6 ml of TEA. The reaction, followed by TLC (eluent: dichloromethane/methanol, 9.2:0.8) is finished after 20 hours. After the various treatments, 12.51 g of a pink oil are obtained, and this is chromatographed on a silica gel column (eluent: dichloromethane/methanol, 96:4). 4.4 g of product are collected. TLC ($CH_2Cl_2$/MeOH 8%). $R_f$: 0.45. Crystallises in an ethyl acetate/petroleum ether or dichloromethane/petroleum ether mixture. M.p. 100°–101° C.

Analysis: $C_{16}H_{22}N_2SO_4$ (338) calculated %: C, 56.80; H, 6.51; N, 8.28; found % : C, 57.00; H, 6.68; N, 8.21.

IR spectrum (KBr) $vcm^{-1}$: 3320–3290 (NH); 1870 ($COCH_3$); 1625 (CONH); 1625 (amide I)

NMR spectrum ($CDCl_3$) δppm: 7.31 (S-5H) benzyl; 6.30 and 5.32 (m-2H) NH; 5.10 (s-2H) benzyl $CH_2$; 3.66 to 2.80 (m-6H) N—$CH_2$ and S—$CH_2$; 2.35 (s-3H) CO—$CH_3$; 2.30 to 1.60 (m-4H) aminobutyryl $CH_2$—$CH_2$.

EXAMPLE 6

N-γ-AMINOBUTYRYL-S-ACETYLCYSTEAMINE HYDROBROMIDE

Prepared according to the general method described above

Reagents used: 1.4 g ($4.1 \times 10^{-3}$ mole) of N-(Z-γ-aminobutyryl)-S-acetylcysteamine. 3 ml of HBr/AcOH.

After lyophilisation in 5 ml of water, 1 g of hygroscopic hydrobromide is collected.

NMR spectrum ($D_2O$) δppm: 3.47 to 3.17 and 3.17 to 2.76 (2m-6H) N—$CH_2$ and S—$CH_2$; 2.50 to 1.66 (m-4H) $CH_2$—$CH_2$; 2.31 (S—3H) $COCH_3$.

EXAMPLE 7

N-(BOC-GLYCYL)-S-ACETYLCYSTEAMINE

General method of coupling using a BOC-AA

A solution of 9 g (0.05 mole) of BOC-glycine in 150 ml of ethyl acetate is stirred at 0° C. with 18 g (0.05 mole) of t-PNC (DCC can also replace t-PNC) in 100 ml of ethyl acetate. After 30 minutes' stirring at 0° C. 7.25 ml of TEA are added and the mixture is left stirring again for 15 minutes. After this time, 9.1 g (0.05 mole) of S-acetylcysteamine hydrochloride are poured into the mixture followed, dropwise, by 11 ml of TEA. The reaction, followed by TLC in a dichloromethane/methanol (9:1) mixture, is finished in 5 hours.

The reaction mixture is then washed with water, then with ice-cold saturated aqueous sodium bicarbonate, again with water, then with an ice-cold 1N aqueous citric acid solution, and finally with water until the pH is neutral. The organic phase is then dried over sodium sulphate and evaporated to dryness under vacuum. 12.5 g of crude product are obtained in the form of an oil. This product is purified by chromatography on a silica gel column (eluent: dichloromethane/methanol, 9.4:0.6). TLC: (dichloromethane/methanol, 9:1) $R_f=0.8$. Detection: UV, iodine vapour or spraying with 10% strength sulphuric acid solution in ethanol, followed by heating the plate. Yld.=40%. Crystallises ( . . . sic) a dicholormethane/petroleum ether mixture. M.p. 59°–60° C.

Analysis: $C_{11}H_{20}N_2SO_4$ (276) calculated %: C, 47.82; H, 7.24; N, 10.14. found %: C, 47.65; H, 7.26; N, 10.04.

NMR spectrum ($CDCl_3$) δppm: 7.20, 5.45 (2m-2H, exchangeable with heavy water) 2NH; 4.07 (d-2H) gly $CH_2$; 3.57 (m-2H) $NHCH_2$; 3.15 (m-2H) S—$CH_2$; 2.35 (S-3H) $COCH_3$; 1.47 (S-9H) tert-butyl.

EXAMPLE 8

N-GLYCYL-S-ACETYLCUSTEAMINE (sic) TRIFLUOROACETATE

General method for deprotection of a BOC-AA with formation of its corresponding trifluoroacetate 2.03 g ($7 \times 10^{-3}$ mole) of N-(BOC-glycyl)-S-acetylcysteamine are stirred at room temperature with 10 ml of TFA and 0.25 ml of thioanisole while the mixture is protected from moisture. The reaction, followed by TLC (eluent: dichloromethane containing 8% of methanol), is finished in 4 hours. The trifluoroacetate is precipitated from the mixture in the form of an oil by adding 150 ml of anhydrous ether, and is washed with $2 \times 150$ ml of ether and then dried in an vacuum desiccator containing phosphoric anhydride and potassium hydroxide flakes. Almost quantitative yield. High purity is obtained by dissolving the salt in 10 ml of distilled water, followed by lyophilisation.

Since they are hygroscopic, these salts are generally stored under vacuum or under an atmosphere of nitrogen. Nevertheless, for this compound, it was possible to crystallise it in an ethyl acetate/petroleum ether (3:1) mixture. M.p. 93°–95° C. IR spectrum (KBr) $cm^{-1}$: several bands indicating the presence of an amine salt, 3340, 3220, 3080, 2995, 2960, 2800, 2740, 2620, 2540, 1700, 1670, (C=O); 1590 (amide).

NMR spectrum ($D_2O$) δppm: 3.70 (S—2H) gly $CH_3$; 3.37 (t-2H) N—$CH_2$; 2.98 (t-2H) S—$CH_2$; 2.29 (S—3H) $COCH_3$.

EXAMPLE 9

N-(BOC-GLYCYL)-S-(DICHLOROACETYL)CYSTEAMINE

Coupling reaction according to the general BOC-AA method

Reagents used: 8.69 g ($49 \times 10^{-3}$ mole) of BOC-glycine in 160 ml of ethyl acetate. 17.3 g ($49 \times 10^{-3}$ mole of t-PNC in 50 ml of ethyl acetate. 7 ml of TEA. 12.34 g ($55 \times 10^{-3}$ mole) of S-(dichloroacetyl)cysteamine hydrochloride.

The mixture is maintained basic by dropwise addition of 11 ml of TEA and the reaction, followed by TLC (eluent: dichloromethane containing 10% of methanol), is finished in 12 hours.

After the treatments already described, 13 g of an oily product are obtained, and this is chromatographed on a silica gel column (elution solvent: dichloromethane containing 3% of methanol). The expected derivative is collected in the form of an oil which crystallises in a dichloromethane/petroleum ether (3:1) mixture. TLC (dichloromethane/methanol, 9:1): $R_f=0.85$.

Analysis: $C_{10}H_{18}N_2SO_3Cl_2$(317) calculated %: C, 37.85; H, 5.67; N, 8.83; found %: C, 37.78; H, 5.69; N, 8.80.

IR spectrum (KBr) $cm^{-1}$: 3320 (NH); 1680 (C=O); 1530 (amide I).

NMR spectrum ($CDCl_3$) δppm: 7.22 and 5.47 (2m-2H) 2NH; 6.0 (S-1H) $CHCl_2$; 4.05 (d-2H) gly $CH_2$; 3.54 (m-2H) N—$CH_2$; 3.13 (m-2H) S—$CH_2$; 1.45 (S-9H) tert-butyl.

EXAMPLE 10

N-GLYCYL-S-(DICHLOROACETYL)CYSTEAMINE TRIFLUOROACETATE

General method for deprotection of a BOC (already described)

Reagents used: 2.2 g ($69 \times 10^{-4}$ mole) of N-(BOC-gly-cyl)-S-(dichloroacetyl)cysteamine. 15 ml of TFA. 0.3 ml of thioanisole.

The reaction, followed by TLC (eluent: dichloromethane containing 10% of methanol), is finished in 3 hours. After the various washes, 1.86 g (yld.=75%) of a colourless oil is collected and this is dissolved in 20 ml of distilled water and lyophilised. This trifluoroacetate then takes the form of a hygroscopic powder.

NMR spectrum ($D_2O$) δppm: 6.15 (S-1H) CH—$Cl_2$; 4.07 (S-2H) gly $CH_2$; from 3.68 to 3.00 (2m-4H) N—$CH_2$—$CH_2$—S.

EXAMPLE 11

Z-GLYCYL-(2-BROMOETHYL)AMINE

First method already described, involving a Z-AA in the presence of a coupling agent and an amine.

Reagents used: 5.2 g ($24 \times 10^{-3}$ mole) of Z-glycine in 50 ml of ethyl acetate. 8.7 g ($25 \times 10^{-3}$ mole) of t-PNC in 25 ml of ethyl acetate. 5 ml of TEA. 9.83 g ($48 \times 10^{-3}$ mole) of 2-bromoethylamine hydrobromide (Fluka), which is released in ethyl acetate by TEA before it is added to the reaction mixture.

The reaction, monitored by TLC (dichloromethane containing 5% of methanol) is no longer proceeding after 5 hours. The various washes are performed and, after evaporation followed by chromatography on a silica gel column (eluent: dichloromethane containing 1.5% of methanol), 3 g of a yellowish oil are obtained, and this is crystallised in a dichloromethane/petroleum ether mixture. Yld.=25%. M.p. 111°–113° C.

Analysis: $C_{12}H_{15}N_2BrO_3$ (315) calculated %: C, 45.71; H, 4.76; N, 8.88; found %: C, 45.68; H, 4.77; N, 8.92.

IR spectrum (KBr) $\nu cm^{-1}$: 3300 (NH); 1680, 1640 (C=O); 1530 (amide I).

NMR spectrum ($CDCl_3$) δppm: 7.33 (S-5H) benzyl; 6.55 and 5.50 (2m-2H, exchangeable with heavy water) 2NH; 5.10 (S-2H) benzyl $CH_2$; 3.88 (d-2H) gly $CH_2$; 3.65 (t-2H) $CH_2Br$; 3.42 (m-2H) N—$CH_2$.

Second method (better yields than the above method)

This involves an activated Z-amino acid.

To a stirred solution at 0° C. of 6.146 g (0.03 mole) of 2-bromoethylamine hydrobromide in 60 ml of DMF, 4.16 ml of TEA is added dropwise. After the addition of the base (20 minutes), 6.12 g (0.02 mole) of the ester Z-glycyl-O-N-succinimide are added to the mixture still at 0° C., and the mixture is then allowed to return to room temperature. The reaction, followed by TLC (eluent: dichloromethane containing 10% of methanol), is finished in 3 hours.

The solvent is evaporated to dryness under vacuum and the residual paste taken up in 400 ml of ethyl acetate. The various washes are then performed: 300 ml of water, then 300 ml of ice-cold saturated aqueous sodium bicarbonate, 300 ml of water, 300 ml of ice-cold aqueous (0.1N) hydrochloric acid and finally water until the pH is neutral. The organic phase is then dried over sodium sulphate and evaporated to dryness under vacuum. A white powder is collected which crystallises in a dichloromethane/petroleum ether mixture. Yld.=5 g, equivalent to 79%. The physicochemical data of this product are identical to those above.

EXAMPLE 12

GYLCYL-(2-BROMOETHYL)AMINE HYDROBROMIDE 3.4 g ($10 \times 10^{-3}$ mole) of Z-glycyl-(2-bromoethyl)amine are treated at room temperature, under an atmosphere of nitrogen and with stirring, with 9 ml of glacial acetic acid saturated with dry hydrobromic acid. The reaction, followed by TLC (eluent: dichloromethane containing 10% of methanol) no longer contains Z after 30 minutes. The hydrobromide is precipitated from the mixture in the form of a paste by adding 100 ml of anhydrous ether, and the mixture is placed at 0° C. for 12 hours.

The crystals formed are drained and dried in a vacuum desiccator over phosphoric anhydride. Yld.=2.4 g, equivalent to 85.7%. M.p. 158°–160° C.

IR spectrum (KBr) $\nu cm^{-1}$: 3400, 3200 ($NH_2$—NH); several bands between 3000 and 2580, indicating the presence of a salt 1660 (C=O); 1570 (amide I).

NMR spectrum ($D_2O$) δppm: 3.74 (S-2H) gly $CH_2$; 3.70 to 3.33 (m-4H) $CH_2$—$CH_2$.

EXAMPLE 13

GYLCYL-(2BROMOETHYL)AMINE HYDROBROMIDE

To a solution of 1.31 g ($5 \times 10^{-3}$ mole) of glycyl-(2-bromoethyl)amine hydrobromide in 10 ml of absolute ethanol, there is added 0.380 g ($5 \times 10^{-3}$ mole) of thiourea solubilised in 8 ml of absolute ethanol. The mixture is brought to boiling for 6 hours and the solvent is then concentrated to ⅓ of its initial volume. On being cooled, crystals are formed which will be filtered off and recrystallised in methanol. Yld.=53%. M.p. 178°–180° C.

NMR spectrum ($D_2O$) δppm: 3.80 (S-2H) gly $CH_2$; 3.66 and 3.40 (2m-4H) $CH_2$—S and NH—$CH_2$.

EXAMPLE 14

N-(Z-GLYCYL)CYSTEAMINE (2 methods of snythesis)

First method

A solution of 2.5 g ($8 \times 10^{-3}$ mole) of N-(Z-glycyl)-S-acetylcysteamine in 40 ml of methanol is treated with 5 ml of sodium methylate (0.263 g of sodium in 5 ml of methanol). The reaction mixture is stirred at room temperature for 1 hour and then brought to pH 1.2 with concentrated hydrochloric acid. The solution is evaporated to dryness under vacuum, and the paste obtained is chromatographed on silica gel (eluent: dichloromethane containing 5% of methanol).

1.5 g of a colourless oil is collected and this crystallises in a mixture of ethyl acetate and petroleum ether. M.p. 95°–96° C. TLC (chloroform/methanol, 9.2:0.8): $R_f$=0.4 (detection by UV or iodine vapour).

Analysis: $C_{12}H_{16}N_2SO_3$ (268) calculated %: C, 53.73; H, 5.97; N, 10.45; found %: C, 53.70; H, 5.86; N, 10.35.

Mass spectrum: $M^+$ 268

IR spectrum (KBr) $\nu cm^{-1}$: 3320, 3280 (NH); 1680, 1650 (C=O); 1540 (amide I).

NMR spectrum ($CDCl_3$) δppm: 7.36 (S-5H) benzyl; 6.83 (m-1H) cysteamine NH (exchangeable by adding $D_2O$); 5.86 (t-1H) gly NH (exchangeable by adding $D_2O$); 5.15 (S—2H) benzyl $CH_2$; 3.86 (d-2H) gly $CH_2$;

3.40 (m-2H) N—CH$_2$, 2.62 (m-2H) S—CH$_2$; 1.38 (t-1H) SH.

Second method

The action of sodium hydrosulphide in methanol on Z-glycyl-(2-bromoethyl)amine leads, after being refluxed for one hour followed by evaporation of the solvent and filtration of the oil obtained on a silica gel column, to the same compound (physicochemical data identical to those above). Yld.=74%.

EXAMPLE 15

DI-Z-N,N'-DIGLYCYLCYSTAMINE (sic)

(3 methods of synthesis)

First method: oxidation of N-(Z-gly-)cysteamine

To a stirred solution of 3.6 g (13×10$^{-3}$ mole) of N-(Z-glycyl)cysteamine in 15 ml of acetic acid and 15 ml of distilled water at room temperature, 20 ml of acetic acid containing 250 mg of iodine are added, and this induces the immediate formation of a precipitate. The reaction mixture is maintained for 15 minutes at room temperature and the precipitate is then filtered, washed with distilled water and then dried in a vacuum desiccator over phosphoric anhydride. The product recrystallises in a mixture of DMF and distilled water. The crystals formed are drained and then washed with a v/v mixture of ethanol and ether, and then with ether. After being dried under vacuum over phosphoric anhydride, the expected derivative is collected in a yield of 40%. M.p. 168°–170° C. TLC (chloroform containing 10% of methanol): R$_f$=0.6.

Analysis: C$_{24}$H$_{30}$N$_4$S$_2$O$_6$ (534) calculated %: C, 53.93; H, 5.61; N, 10.48; found %: C, 54.14; H, 5.73; N, 10.50.

Mass spectrum: M+: 534

IR spectrum (KBr) νcm$^{-1}$: 3320 (NH); 1680, 1635 (C=O); 1535 (amide I)

NMR spectrum (DMSO d$_6$) δppm: 8.12 and 7.44 (2m, exchangeable with heavy water) 2×NH; 7.38 (S) benzyl; 5.05 (S) benzyl CH$_2$; 3.62 (d) gly CH$_2$; 3.50 to 3.10 and 3.10 to 2.58 (2m) N—CH$_2$—CH$_2$—S.

Second method: reaction between Z-glycine and cystamine involving a coupling agent according to the general method already described Reagents used: 7.2 g (34×10$^{-3}$ mole) of Z-gly in 150 ml of ethyl acetate. 12 g (34×10$^{-3}$ mole) of t-PNC (DCC can replace t-PNC) in 50 ml of ethyl acetate. 5.1 ml of TEA. 3.04 g (20×10$^{-3}$ mole) of cystamine in 30 ml of ethyl acetate.

On addition of the cystamine, a precipitate forms immediately. The reaction mixture is stirred at room temperature for 6 hours. The precipitate which contains the expected derivative and triethylamine hydrochloride is drained, washed with 100 ml of ethyl acetate and 100 ml of water, and then recrystallised at approximately 80° C. in DMF containing 10% of distilled water. After filtration and drying in a vacuum desiccator over phosphoric anhydride, 3.1 g of di-Z-N,N'-diglycylcystamine and collected. Yld.=34% (physicochemical criteria identical to those above).

Third method: according to a reaction already described involving an activated ester of an N-protected AA and an amine Reagents used: 2.252 g (0.01 mole) of cystamine dihydrochloride in 20 ml of DMF and 1.70 ml of TEA. 3.06 g (0.02 mole) of Z-glycyl-O-N-succinimide ester in 30 ml of DMF.

The reaction mixture is stirred for 6 hours at room temperature and then evaporated to dryness under vacuum. The residual paste is ground in ethyl acetate, and this induces the formation of a colourless powder which will be filtered off and then washed with distilled water. The residual product crystallises under the same conditions as above. After being filtered and dried, 3.5 g of a product are collected having physicochemical criteria identical to those above.

EXAMPLE 16

N,N'-DIGLYCYLCYSTAMINE DIHYDROBROMIDE

Reaction performed according to the general method already described

Reagents used: 1.8 g (3×10$^{-3}$ mole) of di-Z-N,N'-diglycylcystamine. 12 ml of glacial acetic acid saturated with dry, gaseous hydrobromic acid.

The mixture is stirred for 4 hours at room temperature and 100 ml of anhydrous ether are then added with vigorous stirring, thereby promoting the formation of a pale yellow powder. This powder is drained under vacuum, then washed with 2×50 ml of anhydrous ether and crystallised in a mixture of methanol and ether. After crystallisation and drying in a vacuum desiccator in the presence of phosphoric anhydride and potassium hydroxide, 1.203 g (85%) of dihydrobromide is collected. M.p. 183°–185° C.

NMR spectrum (D$_2$O) δppm: 3.78 (S) gly CH$_2$; 3.55 (t) N—CH$_2$; 2.83 (t) S—CH$_2$.

EXAMPLE 17

DI-BOC-N,N'-DIGLYCYLCYSTAMINE (2 methods)

First method: Reaction between BOC-glycine and cystamine involving a coupling agent according to the general method already described Reagents used: 2.98 g (17×10$^{-3}$ mole) of BOC-glycine in 50 ml of ethyl acetate. 5.92 g (17×10$^{-3}$ mole) of t-PNC (DCC can replace t-PNC). 2.4 ml of TEA. 2.6 g (17×10$^{-3}$ mole) of cystamine in 30 ml of ethyl acetate.

The reaction, monitored by TLC (eluent: dichloromethane containing 5% of methanol), is finished in 6 hours. The conventional washings are performed (water, ice-cold saturated aqueous bicarbonate, water, ice-cold 1N citric acid and water until the pH is neutral). The organic phase is dried over sodium sulphate and then evaporated to dryness under vacuum. The oil collected (impure) is chromatographed on a silica gel column (eluent gradient of a dichloromethane/methanol solution ranging from 2 to 5 % of methanol). 3 g (yld.=37%) of a colourless oil are collected and this crystallises in ethyl acetate. M.p. 97°–98° C. R$_f$(dichloromethane containing 10% of methanol)=0.4.

NMR spectrum (CDCl$_3$) ppm: 7.24 (m, exchangeable with heavy water) NH; 3.82 (d) gly CH$_2$; 3.55 (m) N—CH$_2$; 2.77 (t) S—CH$_2$; 1.42 (S) tert-butyl.

Second method: reaction between BOC-glycine activated by an ester and cystamine

Reagents used: 5.4 g (24×10$^{-3}$ mole) of cystamine dihydrochloride in 50 ml of DMF. 3.4 ml of TEA, 5.44 g (20×10$^{-3}$ mole) of BOC-glycyl-O-N-succinimide ester.

The reaction mixture is stirred for 6 hours at room temperature and treated as above after it has been evaporated to dryness under vacuum and the paste obtained has been taken up in 500 ml of ethyl acetate. The crude product obtained crystallised and homogeneous in TLC does not require chromatography. It will be directly recrystallised in ethyl acetate. Yld.=60% (physicochemical data identical to those above).

EXAMPLE 18

N,N'-DIGLYCYLCYSTAMINE DI(TRIFLUOROACETATE)

Reaction formed according to the general method already described

Reagents used: 1.7 g ($3.6 \times 10^{-3}$ molel) of di-BOC-N,N'-diglycylcystamine. 6 ml of TFA. 0.06 ml of thioanisole.

After 3 hours' stirring at room temperature, the starting material can no longer be distinguished on TLC. There follow the treatments already described and, after lyophilisation, 1.79 g of product is collected in the form of an oil (quantitative yield).

This salt will be stored, like those above, under an atmosphere of nitrogen or under vacuum.

NMR spectrum ($D_2O$) δppm: 3.61 (S) gly $CH_2$; 3.38 (t) N—$CH_2$; 2.66 (t) S—$CH_2$.

EXAMPLE 19

N,N'-DIALANYLCYSTAMINE DIHYDROBROMIDE

The reaction is performed as in Examples 15 and 16, replacing N-(Z-gly-)cysteamine by N-(Z-ala-)cystamine, the molar proportions remaining the same.

After lyophilisation, this product takes the form of an oil.

NMR spectrum ($D_{20}$ (sic)): 4.10 (m) CH; 3.60 (m) N—$CH_2$; 2.90 (t) S—$CH_2$; 1.52 (d) $CH_3$.

EXAMPLES 20 AND 21

N-(BOC-L-ALANYL)-S-ACETYLCYSTAMINE (sic)

1st method, involving the active O-NSu ester of BOC-L-alanine and performed according to the general method described above.

Reagents used: 21.5 g ($75 \times 10^{-3}$ mole) of BOC-L-Ala-ONSu, 200 ml of DMF, 11.6 g of S-acetylcysteamine hydrochloride, 10.45 ml of TEA ($75 \times 10^{-3}$ mole).

The oil obtained after the various washings is purified on a silica column (eluent: acetone/hexane, 4:6). Crystallises in a 1:5 mixture of ether and petroleum ether. M.p. 71°-73° C. TLC (ACOEt) Ef (sic)=0.5. Yld.=42.7%.

Analysis: $C_{12}H_{22}N_2O_4S$ (290): Calculated %: C, 49.65; H, 7.58; N, 9.65; Found %: C, 49.61; H, 7.60; N, 9.62.

NMR spectrum ($CDCl_3$); 6.84(t—1H)NH—$CH_2$; 5.25(d—1H)NH—CH; 4.17 (m—1H)ala. CH; 3.43(m—2H)N—$CH_2$; 3.02(m—2H) S—$CH_2$; 2.33(S—3H)CO—$CH_3$; 1.48(S—9H) tert-butyl H; 1.35(d—3H)ala. $CH_3$.

2nd method. This method is general for coupling between an N-protected amino acid and S-acetylated cysteamine in the presence of a coupling agent.

A solution of 18.9 g (0.1 mole) of BOC-L-Ala in 200 ml of ethyl acetate is stirred at 0° C. with 17.4 g ($5 \times 10^{-2}$ mole) of t-PNC previously dissolved in 100 ml of ethylacetate. After 30 minutes' stirring at 0° C., 14 ml of TEA are added and the mixture is left stirring again for 30 minutes. After this time, 23.3 g (0.15 mole) of S-acetylcysteamine hydrochloride are added to the reaction mixture followed by 21 ml of TEA.

The reaction is followed by TLC in a dichloromethane/methanol (9:1) eluent, and the time required for coupling is approximately 6 hours. The various washings are then performed (water, ice-cold aqueous sodium bicarbonate, water, ice-cold 1% strength hydrochloric acid, water until neutral. After the organic phase is dried over sodium sulphate and evaporated to dryness under vacuum, 11.7 g of a yellow oil are collected. This oil is then chromatographed on a silica column with an eluent consisting of dichloromethane and ether (8:2). 8.3 g of pure product are collected and recrystallised in a mixture of ether and petroleum ether. The physicochemical data of this compound are identical to those above (1st method).

EXAMPLE 22

N-L-ALANYL-S-ACETYLCYSTEAMINE TRIFLUOROACETATE: I 106

Deprotection of N-(BOC-L-alanyl)-S-acetylcysteamine is carried out according to the general method. Reagents used: 5.7 g ($19 \times 10^{-3}$ mole) of BOC, 9.3 ml of TFA.

The reaction, followed by TLC, is finished in 90 minutes. After the various washings with ether, the trifluoroacetate is taken up in distilled water and then lyophilised. 4.45 g of a gum are collected. NMR spectrum ($D_2O$) δppm: 3.95 (q—1H) ala; 3.40 (m—2H)N—$CH_2$; 2.98 (m—2H)S—$CH_2$; 2.31 (S—3H)CO—$CH_3$; 1.38 (d—3H) ala $CH_3$.

EXAMPLE 23

2-(BOC-GLYCYLTHIO)-1,1-DIMETHYL-1-ACETAMIDOETHANE

The 1-thioacetamido-2-methyl-2-aminopropane hydrobromide required for the following reactions is obtained according to the method below:

A solution of 4.56 g ($4 \times 10^{-2}$ mole) of potassium thioacetate in 100 ml of DMF is stirred at 0° C. for 20 minutes, and 9.32 g ($4 \times 10^{-2}$ mole) of 1-bromo-2-methyl-2-aminopropane hydrobromide (J. E. EARLEY et al., J. Amer. Chem. Soc., 1958, 80, 3458) are added. The solution is allowed to return to room temperature and stirring is maintained for 12 hours. The solvent is then evaporated to dryness under vacuum at a temperature below 60° C. The residual paste is taken up in acetonitrile and this precipitates potassium bromide and the residual potassium thioacetate, which will be filtered off. On evaporation of the organic phases, 8.8 g of thioacetamide derivative are collected in the form of a yellow gum. Proton NMR analysis of this gum reveals the presence of approximately 5% of the starting brominated derivative; nevertheless, the impure gum will be used for the subsequent reactions in which purification by chromatography or recrystallisation is required.

Two methods are possible to obtain 2-(BOC-glycylthio)-1,1-dimethyl-1-acetamidoethane:

1st method, involving the active O-NSu ester of BOC-glycine, and carried out according to the general method: Reagents used: 272 mg ($10^{-3}$ mole) of BOC-gly-ONSu, 10 ml of DMF, 280.1 mg ($1.23 \times 10^{-3}$ mole) of 1-thioacetamido-2-methyl-2-aminopropane hydrobromide, 0.171 ml of TEA.

After the various treatments, the expected derivative is obtained in a 40% yield. Recrystallises in a mixture of ethyl acetate and petroleum ether. M.p. 134°-136° C. TLC: Rf=0.4 (ethyl acetate/petroleum ether, 8:2 v/v).

Analysis: $C_{13}H_{24}N_2O_4S$ (304) Calculated %: C, 51.31; H, 7.89; N, 9.21; Found %: C, 51.32; H, 7.84; N 9.23

IR spectrum (KBr) cm$^{-1}$: 3340–3280 (NH); 3100-29-80-2940 (CH—CH$_2$—CH$_3$); 1695–1685–1640 (C=O); 1570–1535 (amide I).

NMR spectrum (CDCl$_3$) δppm: 5.73(S—1H)N-H—COCH$_3$; 5.35 (m—1H)gly NH; 4.10(d—2H)gly CH$_2$; 3.40(S—2H) S—CH$_2$; 1.90(S—3H)CO—CH$_3$; 1.48 (S—9H) tert-butyl H; 1.37(S—6H) C—(CH$_3$)$_2$.

2nd method, involving N-protected glycine and 1-thioacetamido-2-methyl-2-aminopropane hydrobromide in the presence of a coupling agent (DCC).

Reagents used: 6.75 g ($3.86 \times 10^{-2}$ mole) of BOC-gly, 40 ml of DMF, 8.8 g ($\approx 3.8 \times 10^{-2}$ mole) of 1-thioacetamido-2-methyl-2-aminopropane hydrobromide, 6.65 ml of DIEA, 7.95 g ($3.85 \times 10^2$ (sic) mole) of DCC. Reaction time: 6 hours.

After filtration of the DCU formed and evaporation of the DMF, the paste obtained is taken up in ethyl acetate and the various washings are performed. After evaporation of the organic phases, 4.6 g of a compound are collected which compound is in every way identical to that above (TLC, IR, NMR).

EXAMPLE 24

2-GLYCYLTHIO-1,1-DIMETHYL-1-ACETAMIDOETHANE TRIFLUOROACETATE: I 107

Deprotection of 2-(BOC-glycylthio)-1,1-dimethyl-1-acetamidoethane is carried out according to the general method.

Reagents used: 1.9 g ($6.2 \times 10^{-3}$ mole) of BOC, 6 ml of TFA.

The reaction, followed by TLC (dichloromethane/methanol: 9:1 v/v) is finished in 90 minutes and, after being precipitated by addition of anhydrous ether, compound I 107 is recrystallized in a mixture of methanol and ether. 1.9 g of trifluoroacetate is collected. M.p. 165° C.

IR spectrum (KBr) νcm$^{-1}$: 3300–3260 (NH); 3080–3000–2950 (CH—CH$_2$—CH$_3$); several bands between 2950 and 2500, in particular 2740–2660, indicate the presence of the trifluoroacetate; 1690–1645 (C=O); 1565 (amide I).

NMR spectrum (D$_2$O) δppm: 4.13(s—2H)gly CH$_2$; 3.50(S—2H)S—CH$_2$; 1.88(S—3H)CO—CH$_3$; 1.29(S—6H)C—(CH$_3$)$_2$.

EXAMPLE 25

2-(BOC-GLYCYLAMINO)-2,2-DIMETHYL-1-(THIOACETYL)ETHANE

The synthesis of this compound is carried out according to the general method involving N-protected glycine and 1-thioacetamido-2-methyl-2-aminopropane hydrobromide in the presence of a coupling agent (t-PNC).

Reagents used: 4.53 g (2.5 g (sic)$\times 10^{-2}$ mole) of BOC-gly, 50 ml of ethyl acetate, 4.51 g ($12.9 \times 10^{-3}$ mole) of t-PNC, 3.61 ml of TEA, 5.9 g ($2.59 \times 10^{-2}$ mole) of 1-thioacetamido-2-methyl-2-aminopropane hydrobromide, 3.61 ml of TEA.

The reaction, followed by TLC is finished in 8 hours. The conventional washings are then carried out and, after evaporation of the organic phases, an oily product is collected which is purified by chromatography on a silica column using a mixture of eluents consisting of ethyl acetate and dichloromethane (6:4 v/v). The purified product again takes the form of an oil ($\approx 2$ g). TLC (CH$_2$Cl$_2$/MeOH, 4:6 v/v): R$_f$=0.6.

Analysis: $C_{13}H_{24}N_2O_4S$ (304) Calculated %: C, 51.31; H, 7.89; N, 9.21; Found %: C, 51.29; H, 7.90; N, 9.24.

NMR spectrum (CDCl$_3$) δppm: 6.57(S—1H)N-H—C—; 5.70 (m—1H)gly NH; 3.66 (m—2H)gly CH$_2$; 3.34(S—2H) S—CH$_2$; 2.33(S—3H) CO—CH$_3$; 1.50 to 1.10(m—15H) C—(CH$_3$)$_2$ and tert-butyl H.

EXAMPLE 26

2-GLYCYLAMINO-2,2-DIMETHYL-1-(THIOACETYL)ETHANE TRIFLUOROACETATE: I 108

Deprotection of 2-(BOC-glycylamino)-2,2-dimethyl-1-(thioacetyl)ethane is carried out according to the general method:

Reagents used: 1.9 g ($6.2 \times 10^{-3}$ mole) of 2-(BOC-glycylamino)-2,2-dimethyl-1-(thioacetyl)ethane, 6 ml of TFA.

The reaction, followed by TLC, is finished in 60 minutes, and since it does not crystallise after the treatments with anhydrous ether, the compound I 108 will be taken up in distilled water and then lyophilised. 1.8 g of a pale yellow oil is collected.

NMR (D$_2$O) spectrum δppm: 3.50(S—2H)gly CH$_2$; 3.16 (S—2H)S—CH$_2$; 2.19(S—3H)CO—CH$_3$; 1.13(S—6H)C—(CH$_3$)$_2$.

EXAMPLE 27

N-(BOC-GLYCYLGLYCYL)-S-ACETYLCYSTEAMINE

The production of this compound is carried out according to the general method involving N-protected glycylglycine and S-acetylcysteamine hydrochloride in the presence of t-PNC as coupling agent.

Reagents used: 7 g ($3.02 \times 10^{-2}$ mole) of BOC-glygly, 70 ml of THF, 10.5 g ($3.02 \times 10^{-2}$ mole) of t-PNC, 4.21 ml ($3.02 \times 10^{-2}$ mole) of TEA, 4.7 g ($3.02 \times 10^{-2}$ mole) of S-acetylcysteamine hydrochloride.

The reaction is dealt with after 8 hours' stirring. The THF is evaporated to dryness under reduced pressure, the residue is taken up in ethyl acetate and the various washings are carried out. After evaporation of the organic phases, there are collected 12 g of an oily mixture which is impure in TLC. The coupling product is isolated pure after being chromatographed twice on a silica gel column using ethyl acetate as eluent. 2.5 g (24.8%) of an oil are collected and this crystallises in a mixture of ethyl acetate and petroleum ether.

M.p. 109°–111° C. TLC (CH$_2$Cl$_2$/MeOH, 9:1 v/v): R$_f$=0.3.

Analysis: $C_{13}H_{23}N_3O_5S$ (333), Calculated %: C, 46.84; H, 6.90; N, 12.61; Found %: C, 46.84; H, 6.92; N, 12.58.

IR spectrum (KBr) νcm$^{-1}$: 3290 (NH); 3070-29-80-2950 (CH—CH$_2$—CH$_3$); 1680–1640 (C=O); 1550 (amide I).

NMR spectrum (CDCl$_3$) δppm: 7.53 (m—2H)gly 2NH; 5.80 (m—1H) NH(cysteamine); 3.88 (dd—4H)gly CH$_2$; 3.35(m—2H) N—CH$_2$ (cysteamine); 2.98(m—2H)S—CH$_2$; 2.34(S—3H)CO—CH$_3$; 1.44(S—9H) tert-butyl H.

EXAMPLE 28

N-GLYCYLGLYCYL-S-ACETYLCYSTEAMINE TRIFLUOROACETATE: I 109

Deprotection of N-(BOC-glycylglycyl)-S-acetylcysteamine is carried out according to the general method:

Reagents used: 1.05 g ($3.15 \times 10^{-3}$ mole) of BOC, 6 ml of TFA.

The reaction, followed by TLC, is finished in 90 minutes and, after being precipitated by addition of anhydrous ether, the compound I 109 is recrystallised in a mixture of methanol and ether. 1.100 g of trifluoroacetate is collected, m.p. 117°–118° C.

IR spectrum (KBr) $\nu cm^{-1}$: 3300(NH); 3130-30-90-2960 (CH—CH$_2$—CH$_3$); several bands between 2980 and 2350, in particular 2880-2760-2600-2370, indicate the presence of the trifluoroacetate; 1680-1650 (C=O); 1540 (amide I).

NMR spectrum (D$_2$O) δppm: 3.78 and 3.75 (2S—4H) gly CH$_2$; 3.26 (m—2H) N—CH$_2$; 2.90 (m—2H) S—CH$_2$; 2.23 (S—3H) CO—CH$_3$.

EXAMPLE 29

3-(BOC-GLYCYLAMINO)-1-BROMO-2-PROPANOL

This is obtained according to the general method and involves the O-NSu ester of N-protected glycine and also 1-bromo-3-amino-2-propanol hydrobromide described by D. M. BALL et al., J. Org. Chem. 1963, 28, 1580.

Reagents used: 9.21 g ($3.38 \times 10^{-2}$ mole) of BOC-gly-ONSu, 100 ml of DMF, 7.95 g ($3.38 \times 10^{-2}$ mole) of 1-bromo-3-amino-2-propanol hydrobromide, 4.75 ml ($3.38 \times 10^{-2}$ mole) of TEA.

The reaction, followed by TLC, is finished in 6 hours. The DMF is then evaporated to dryness under vacuum. The residual gum is taken up in ethyl acetate and the various washings are carried out. After evaporation of the solvents, 6.20 g of an oil are collected and this recrystallises in a mixture of ethyl acetate and petroleum ether. M.p. 94°–96° C. TLC (CH$_2$Cl$_2$/MeOH, 9:1 v/v): R$_f$=0.5 (detection by iodine vapour or by heating the plate to a temperature >200° C.).

Analysis: C$_{10}$H$_{19}$N$_2$BrO$_4$ (311) Calculated %: C, 38.58; H, 6.10; N, 9.00; Found %: C, 38.61; H, 6.08; N, 9.03.

IR spectrum (KBr) $\nu cm^{-1}$: 3380(NH—OH) broad band; 2980-2940(CH—CH$_2$); 1690 (C=O); 1525 (amide I).

NMR spectrum (CDCl$_3$) δppm: 7.10 and 5.66 (2m—2H), 2NH; 4.45 to 3.30 (3m—8H)gly CH$_2$, CH$_2$—CH, CH—OH, CH$_2$Br; 1.47(S—9H) tert-butyl H.

EXAMPLE 30

3-(BOC-GLYCYLAMINO)-2-ACETOXY-1-(THIOACETYL)PROPANE and

1,2-DI[3-(BOC-GLYCYLAMINO)-2-ACETYLOXYPROPYL]DISULPHIDE

A stirred (sic) solution of 1.01 g ($8.8 \times 10^{-3}$ mole) of potassium thioacetate in 20 ml of DMF is stirred at 0° C. for 15 minutes, and 2.10 g ($6.7 \times 10^{-3}$ mole) of 3-(BOC-glycylamino)-1-bromo-2-propanol are added. The reaction mixture is maintained at 0° C. for 2 hours and then left for 10 hours at room temperature. The solvent is then evaporated to dryness under vacuum and the residual paste co-evaporated with petroleum ether. Using TLC with double coloration in ether, the presence is noted of several spots, in particular the two expected products and a third product which is positive in the sodium nitroprusside test. This is hence a derivative containing a thiol. Since the three products are difficult to separate by chromatography on a silica column, we subjected the entire paste obtained above to oxidation in methanol in the presence of iodine and sodium acetate. The iodine is added until there is persistent coloration of the solution. TLC of this medium now only shows two spots which are negative to the SH test.

The mixture is then evaporated to dryness under vacuum, taken up in ethyl acetate and washed with sodium thiosulphate and then water. The organic phases are combined, dried over sodium sulphate and evaporated to dryness under vacuum. Approximately 2 g of a colourless oil are collected and this will be chromatographed on a silica column with an eluent consisting of a mixture of dichloromethane and ether (6:4 v/v).

The less polar compound in TLC (eluent: CH$_2$Cl$_2$/MeOH, 9:1 v/v), R$_f$=0.8, was identified as 3-(BOC-glycylamino)-2-acetoxy-1-(thioacetyl)propane. Isolated in the form of an oil, this product crystallises in a mixture of ethyl acetate and hexane. M.p. 74°–76° C.

Analysis: C$_{14}$H$_{24}$N$_2$O$_6$S (348) Calculated %: C, 48.27; H, 6.89; N, 8.04; Found %: C, 48.29; H, 6.85; N, 8.07.

IR spectrum (KBr) $\nu cm^{-1}$: 3330-3260(NH); 3080-2980-2940 (CH—CH$_2$—CH$_3$); 1740-1690-1650 (C=O); 1520-1510 (amide I).

NMR spectrum (CDCl$_3$) δppm: 6.93 and 5.53 (2m—2H)2NH; 4.98(m—1H)CH; 3.80(d—2H) gly CH$_2$; 3.48(m—2H)N—CH$_2$; 3.13(m—2H)S—CH$_2$; 2.33(S—3H)S—COCH$_3$; 2.07(S—3H)O—CO—CH$_3$; 1.48(S—9H) tert-butyl H.

The more polar compound in TLC (same eluent as above) has an R$_f$ value of 0.75, and was identified as 1,2-di[3-(BOC-glycylamino)-2-acetoxypropyl]disulphide. This product was obtained in the form of an oil.

Analysis: C$_{24}$H$_{42}$N$_4$O$_{10}$S$_2$ (610) calculated %: C, 47.21; H, 6.68; N, 9.18; found %: C, 47.23; H, 6.84; N, 9.22.

NMR spectrum (CDCl$_3$) δppm: 7.12 and 5.80 (2m—4H)NH; 5.16(m—2H)CH; 3.80(d—4H) gly CH$_2$; 3.56(m—4H)N—CH$_2$; 2.93(d—4H)S—CH$_2$; 2.06(S—6H)O—CO—CH$_3$; 1.33(S—18H) tert-butyl H.

It was possible to isolate from the mixture, before the oxidation by iodine, and to identify, a sample of the derivative possessing a free thiol. This was indeed 3-(BOC-glycylamino)-2-acetoxy-1-propanethiol.

NMR spectrum (CDCl$_3$) δppm: 7.13 and 5.84 (2m—2H)NH; 4.90(m—1H)CH; 3.80(d—2H) gly CH$_2$; 3.59(m—2H)N—CH$_2$; 2.72 (m—2H)S—CH$_2$; 2.06(S—3H)O—CO—CH$_3$; 1.70 (t—1H)SH; 1.46 (S—9H) tert-butyl H.

EXAMPLE 31

1,2-DI(3-GLYCYLAMINO-2-ACETOXYPROPYL)-DISULPHIDE DI(TRIFLUOROACETATE): I 110

Deprotection of 1,2-di[3-(BOC-glycylamino)-2-acetoxypropyl]disulphide is carried out according to the general method.

Reagents used: 940 mg ($1.5 \times 10^{-3}$ mole) of 1,2-di[3-(BOC-glycylamino)-2-acetoxypropyl]disulphide; 8 ml of TFA.

The reaction, followed by TLC, is finished in 90 minutes and, since it does not crystallise after the washings with anhydrous ether, the compound will be lyophilised. 859.4 mg of an oil are collected (yld.=87.4%).

NMR spectrum (D$_2$O) δppm: 4.96(m—2H)CH; 3.60(S—4H) gly CH$_2$; 3.33(m—4H)N—CH$_2$; 2.74(d—4H)S—CH$_2$; 1.88(S—6H)O—CO—CH$_3$.

EXAMPLE 32

3-GLYCYLAMINO-2-ACETOXY-1-(THIOACETYL)PROPANE TRIFLUOROACETATE: I 111

Deprotection of 3-(BOC-glycylamino)-2-acetoxy-1-(thioacetyl)propane is carried out according to the general method.

Reagents used: 1.4 g (4×10$^{-3}$ mole) of 3-(BOC-glycylamino)-2-acetoxy-1-(thioacetyl)propane, 6 ml of TFA.

The reaction, followed by TLC, is finished in 90 minutes and, since it does not crystallise after the washings with anhydrous ether, the compound I 111 will be lyophilised. 1.383 g of an oil (yld.=95.5%) is collected.

NMR spectrum (D$_2$O) δppm: 5.01(m—1H)CH; 3.80(S—2H) gly CH$_2$; 3.49(m—2H)N—CH$_2$; 3.13(m—2H)S—CH$_2$; 2.28(S—3H)S—COCH$_3$; 2.08(S—3H)O—CO—CH$_3$.

EXAMPLE 33

S-(BOC-GLYCYL)-N-ACETYLCYSTEAMINE

A solution containing 7 g (4×10$^{-2}$ mole) of BOC-glycine in 60 ml of DMF is stirred and cooled to 0° C., and 8.24 g (4×10$^{-2}$ mole) of DCC are then added. 6.22 g (4×10$^{-2}$ mole) of S-acetylcysteamine hydrochloride are then added to the mixture at 0° C., and a solution of 5.56 ml of TEA in 20 ml of DMF is then added dropwise. After the TEA has been added, the mixture is allowed to return to room temperature and stirring is continued for 12 hours. The precipitate of DCU formed is drained and the filtrate is concentrated to dryness under vacuum. The residual paste is taken up in ethyl acetate and the various washings of the solution are carried out: water; ice-cold saturated aqueous sodium bicarbonate; water; 1N aqueous citric acid; water until neutral. The organic phases are combined, dried over sodium sulphate and evaporated to dryness under vacuum.

An oil is collected which is impure in TLC (eluent: ethyl acetate). Two spots with R$_f$0.4 and 0.25 predominate. Two products are separated by chromatography on a silica column (eluent: CH$_2$Cl$_2$ containing 2% of methanol). The less polar compound (R$_f$0.4), 3 g, was isolated and identified as N-(BOC-glycyl)-S-acetylcysteamine.

The more polar compound (R$_f$0.25) was collected in the form of an oil (2.55 g) which recrystallises in a mixture of ethyl acetate and petroleum ether. M.p. 120° C.

Analysis: C$_{11}$H$_{20}$N$_2$SO$_4$ (276) Calculated %: C, 47.82; H, 7.24; N, 10.14; Found %: C, 47.79; H, 7.26; N, 10.16.

IR spectrum (KBr) νcm$^{-1}$: 3340-3260(NH): 3060-3000-2960 (CH—CH$_2$—CH$_3$); 1695-1660 (C=O); 1550 (amide I).

NMR spectrum (CDCl$_3$) δppm: 7.22 and 6.28 (2m—2H)NH; 4.14(d—2H)gly. CH$_2$; 3.48(m—2H)N—CH$_2$; 3.26 (m—2H)—S—CH$_2$; 2,10(S—3H)CO—CH$_3$; 1.58 (S—9H)tert-butyl H.

EXAMPLE 34

S-GLYCYL-N-ACETYLCYSTEAMINE TRIFLUOROACETATE: I 114

Deprotection of S-(BOC-glycyl)-N-acetylcysteamine is carried out according to the general method.

Reagents used: 2.072 g (7.5×10$^{-3}$ mole) of BOC. 3 ml of TFA.

The reaction, followed by TLC, is finished in 2 hours, after having been washed with anhydrous ether, compound I 114 is taken up in distilled water and then lyophilised. 2.1 g of a yellow oil are collected. Yld.=96%.

NMR spectrum (D$_2$O) δppm: 4.12(S—2H)gly. CH$_2$, from 3.58 to 2.83 (m—4H)S—CH$_2$—CH$_2$—N; 1.92 (S—3H)CO—CH$_3$.

EXAMPLE 35

DI-BOC-N,N'-DI(GLYCYLGLYCYL)CYSTAMINE

Of the three methods envisaged, and carried out, in scheme 5, there will only be described that which has provided compound in the best yields according to the general method which involves an activated ester of a dipeptide and cystamine.

Reagents used: 1.194 (5.3×10$^{-3}$ mole) of cystamine dihydrochloride in 40 ml of DMF and 1.48 ml of TEA. 3.5 g of Boc-glycylglycyl-O-N-succinimide ester.

The reaction mixture is stirred for 12 hours at room temperature and then evaporated to dryness under vacuum. The residual paste is taken up in ethyl acetate. The conventional washings are then carried out (water, ice-cold saturated aqueous sodium bicarbonate, water, 1% strength HCl, water until the pH is neutral). The organic phase is dried over sodium sulphate and then evaporated to dryness under vacuum. 2.3 g of a colourless powder are collected and this recrystallises in a mixture of ethyl acetate and petroleum ether. M.p. 118°–120° C. R$_f$ (butanol/ethanol/water, 2:1:1 v/v/v)=0.8.

Analysis: C$_{22}$H$_{40}$N$_6$S$_2$O$_8$ (580) Calculated %: C, 45.51; H, 6.89; N, 14.48; Found %: C, 45.49; H, 6.91; N, 14.48.

NMR spectrum (DMSO) δppm: 7.40 and 5.80 (2m—6H) 6NH; 4.0 (2d—8H)gly CH$_2$; 3.53 (m—4H) N—CH$_2$; 2.95 (m—4H) S—CH$_2$; 1.44 (S—18H)tert-butyl.

EXAMPLE 37

N,N'-DI(GLYCYLGLYCYL)CYSTAMINE DI(TRIFLUOROACETATE) I 116

Reaction performed according to the general method already described.

Reagents used: 2.3 g (3.9×10$^3$ mole) of di-Boc-N,N'-di(glycylglycyl)cystamine. 6 ml of TFA.

After 2 hours' stirring at room temperature, the starting material can no longer be distinguished on TLC. The treatments already described are then carried out and, after lyophilisation, 2.22 g of product are collected in the form of an oil (Yld.=93.6%).

This salt will be stored under an atmosphere of nitrogen or under vacuum.

NMR spectrum (D$_2$O) δppm: 3.95 and 3.86 (2S-8H)gly CH$_2$; 3.51 (m-4H) N—CH$_2$; 2.93 (m-4H) S—CH$_2$.

EXAMPLE 37

BOC-GLYCYL-[2-METHYL-2-(ACETYLMER-CAPTO)ETHYL]AMINE

A stirred solution of 6.8 g ($25 \times 10^{-3}$ mole) of Bos-glycyl-O-N-succinimide ester in 100 ml of acetonitrile is cooled to 0° C., and 4.23 g ($25 \times 10^{-3}$ mole) of 2-methyl-2-(acetylmercapto)ethylamine hydrochloride are added, followed by a solution of 3.48 ml ($25 \times 10^{-3}$ mole) of triethylamine in 10 ml of acetonitrile added dropwise. The reaction temperature is maintained at 0° C. throughout the addition of TEA, the mixture is allowed to return to room temperature and stirring is continued for 8 hours. The solution is then evaporated to dryness under vacuum. The white residue is taken up in dichloromethane and the various washings are carried out (water, ice-cold saturated aqueous sodium bicarbonate, water, 10% strength citric acid in water, water) until the pH is neutral. The organic phase are combined, dried over sodium sulphate and evaporated to dryness under vacuum. 7.6 g of crude product are obtained and this will be chromatographed on a silica gel column using an eluent consisting of a mixture of benzene and ethyl acetate (7:3 v/v). After crystallisation in a mixture of ether and hexane or ethyl acetate and petroleum ether, 1.38 g of colourless crystals is collected.

TLC (benzene/ethyl acetate, 5:5): $R_f=0.3$.
Yld. = 19%. M.p. 70°–73° C.

Analysis: $C_{12}H_{22}N_2SO_4$ (290) Calculated %: C, 49.65; H, 7.58; N, 9.65; Found %: C, 49.63; H, 7.54; N, 9.62.

IR spectrum (KBr) $\nu cm^{-1}$: 3360, 3320 (NH); 2990, 2923 (CH—CH$_2$); 1685, 1660 (C=O); 1525 (amide I).

NMR spectrum (CDCl$_3$) δ ppm: 6.70 and 5.40 (2m-2H) 2NH; 3.78 (d-2H)gly CH$_2$; 3.43 (m-3H) N-CH$_2$-CH; 2.33 (S—3H) COCH$_3$; 1.46 (S-9H)tert-butyl; 1.29 (d-3H) CH$_3$.

EXAMPLE 38

GLYCYL-[2-METHYL-2-(ACETYLMERCAP-TO)ETHYL]AMINE TRIFLUOROACETATE: I 118

General method for deprotecting a BOC (already described). Reagents used: 1.38 g ($47 \times 10^{-3}$ mole) of BOC-glycyl-[2-methyl-2-(acetylmercapto)ethyl]amine. 7 ml of TFA.

The reaction, followed by TLC until the BOC has disappeared, is finished in 2 hours. The reaction mixture is then evaporated to dryness under vacuum and the oil obtained is taken up in 50 ml of distilled water. The aqueous phase, washed with dichloromethane (3×50 ml) and then lyophilised, provides 1.38 g of trifluoroacetate in the form of a hygroscopic oil. Yld. = 97.18%. NMR spectrum (D$_2$O) δ ppm: 3.69 (S-2H)gly CH$_2$; from 3.65 to 3.15 (2m-3H) N—CH$_2$—CH; 2.28 (S—3H) COCH$_3$; 1.20 (d-3H) CH$_3$.

EXAMPLE 39

N-(BOC-SARCOSYL)-S-ACETYLCYSTEAMINE

Reaction between BOC-sarcosine and S-acetylcysteamine involving a coupling agent according to the general method already described.

Reagents used: 9.58 g ($50.7 \times 10^{-3}$ mole) of BOC-sarcosine in 70 ml of acetonitrile. 8.82 g ($25.3 \times 10^{-3}$ mole) of t-PNC in 90 ml of acetonitrile. 7.08 ml ($50.7 \times 10^{-3}$ mole) of TEA. The mixture is stirred at 0° C. for 15 minutes and 8.97 g ($57 \times 10^{-3}$ mole) of S-acetylcysteamine hydrochloride are added followed by a solution of 10.86 ml ($77 \times 10^{-3}$ mole) of TEA in 30 ml of acetonitrile.

The reaction mixture is stirred for 12 hours at room temperature and then evaporated to dryness under vacuum. The residue is taken up in 400 ml of dichloromethane and the various washings are carried out (water, ice-cold saturated aqueous sodium bicarbonate, water, 10% strength citric acid in water, water until the pH is neutral). The organic phase, dried over sodium sulphate and then evaporated to dryness under vacuum, provides 11.9 g of crude product which will be chromatograhed on a silica gel column using an eluent consisting of a mixture of ethyl acetate containing 20% of petroleum ether. After crystallisation in a mixture of ethyl acetate and petroleum ether, 5.52 g of colourless crystals are collected. TLC (ethyl acetate containing 20% of petroleum ether): $R_f=0.5$. Yld. = 37.6%. M.p. 77°–79° C.

Analysis: $C_{12}H_{22}N_2SO_4$ (290) Calculated %: C, 49.65; H, 7.58; N, 9.65; Found %: C, 49.62; H, 7.61; N, 9.67.

IR spectrum (KBr) $\nu cm^{-1}$ = 3270 (NH); 3080, 2980, 2930 (CH—CH$_2$); 1700, 1655 (C=O); 1560 (amide).

NMR spectrum (CDCl$_3$) δ ppm: 6.50 (m-1H) NH; 3.88 (S-2H) gly CH$_2$; 3.47 (m-2) N—CH$_2$; 3.04 (m-2H) S—CH$_2$; 2.93 (S-3H) N—CH$_3$; 2.36 (S-3H) COCH$_3$; 1.50 (S-9H)tert-butyl.

EXAMPLE 40

N-SARCOSYL-S-ACETYLCYSTEAMINE TRIFLUOROACETATE I 123

General method for deprotecting a BOC (already described). Reagents used: 2 g ($6.8 \times 10^{-3}$ mole) of N-(BOC-sarcosyl)-S-acetylcysteamine. 7 ml of TFA. The reaction, followed by TLC, is finished in 2 hours. After the various washings, 1.87 g of colourless powder is collected. Yld. = 89.6%. M.p. = 91°–93° C.

IR spectrum (KBr) $\nu cm^{-1}$: several bands indicating the presence of an amine salt, 3240, 3090, 2975, 2840, 2620, 2260; 1700; 1670 (C=O); 1580 (amide).

NMR spectrum (D$_2$O) δ ppm: 3.83 (S-2H)gly CH$_2$; 3.47 (m-2H) N—CH$_2$; 3.06 (m-2H) S—CH$_2$; 2.75 (S-3H) N—CH$_3$; 2.39 (S-3H) COCH$_3$.

EXAMPLE 41

DI-BOC-N,N'-DISARCOSYLCYSTAMINE

Reaction performed according to the general method already described which involves an activated ester of BOC-sarcosine and cystamine.

Reagents used: 3.15 g ($14 \times 10^{-3}$ mole) of cystamine dihydrochloride in 50 ml of DMF and 3.9 ml of TEA. 7.15 g ($25 \times 10^{-3}$ mole) of BOC-sarcosyl-O-N-succinimide ester.

The reaction mixture is stirred for 12 hours at room temperature and then evaporated to dryness under vacuum. The residual paste is taken up in 200 ml of distilled water and the white precipitate formed is drained and then crystallised in a mixture of ethyl acetate, methanol and petroleum ether. 4.5 g of the expected compound are collected. Yld. = 65%. M.p. = 178°–180° C.

TLC (dichloromethane containing 5% of methanol): $R_f=0.3$.

Analysis: $C_{20}H_{38}N_4S_2O_6$ (494) Calculated %: C, 48.58; H, 7.69; N, 11.33; Found %: C, 48.54; H, 7.66; N, 11.35.

IR spectrum (KBr) $cm^{-1}$: 3270 (NH); 3080, 2980, 2930 (CH—CH$_2$); 1700, 1660 (C=O); 1560 (amide).

NMR spectrum (DMSO) ppm: 8.15 (t-2H) NH; 384 (S-4H)gly CH$_2$; 3.42 (m-4H) N—CH$_2$; 2.86 (m-4H) S-CH$_2$; 286 (S-6H) CH$_3$; 1.42 (S-18H)tert-butyl.

EXAMPLE 42

N,N'-DISARCOSYLCYSTAMINE DI(TRIFLUOROACETATE): I 124

General method for deprotecting a BOC (already described). Reagents used: 2 g (4×10$^{-3}$ mole) of di-BOC-N,N'-disarcosylcystamine. 7 ml of TFA. The reaction, followed by TLC, is finished in 1 hour. After the various washings, 1.96 g of colourless hygroscopic powder is collected. Yld.=93.8%.

NMR spectrum (D$_2$O) δ ppm: 3.83 (S-4H) gly. CH$_2$; 3.52 (t-4H) N—CH$_2$; 2.83 (t-4H) S—CH$_2$; 2.75 (S—6H) CH$_3$.

EXAMPLE 43

2-(GLYCYLAMINO)ETHYLTHIOSULPHURIC ACID: I 125

A solution, containing 1.31 g (5×10$^{-3}$ mole) of glycyl(2-bromoethyl)amine hydrobromide, 1.24 g (5×10$^{-3}$ mole) of sodium thiosulphate 5 H$_2$O, 0.68 g (5×10$^{-3}$ mole) of sodium acetate 3 H$_2$O, and 6 ml of distilled water, is heated to 90°–95° C. until the starting bromide has disappeared. The reaction is followed by TLC (butanol/ethanol/water, 2:1:1 v/v/v). R$_f$ of the bromide 0.7. (In the same eluent, R$_f$ of the expected compound 0.15). The reaction time is approximately 2 hours. On addition of ethanol, an oil appears. The supernatant is decanted, the oil is redissolved in the minimum quantity of distilled water and ethanol added again. This procedure of washing the oil is repeated 5 times. The oily phase obtained is then taken up in distilled wter and decolourised with animal charcoal. The colourless solution is then lyophilised and provides a hygroscopic powder which still contains sodium thiosulphate.

The pure product will be isolated after filtration on a silica gel column using a gradient of eluents consisting of acetonitrile and water. Yld.=40%. This compound will be stored under an atmosphre of nitrogen. NMR spectrum (D20): 3.85 (S-2H) gly. CH$_2$; 3.63 (m-2H) N—CH$_2$; 3.25 (m-2H) SCH$_2$.

EXAMPLE 44

SODIUM S-(2-GLYCYLAMINOETHYL)PHOSPHOROTHIOATE: I 126

To 9.4 ml of water stirred at 15°–20° C., 1.714 g (9.52×10$^{-3}$ mole) of sodium phosphorothioate* is added while the temperature is maintained. A white suspension is obtained. 2.5 g (9.54×10$^{-3}$ mole) of glycyl-(2-bromoethyl)amine hydrobromide are then added. When the mixture has become homogeneous (1 hour), 4.7 ml of DMF are added dropwise while the temperature is still maintained at between 15° and 20° C. Stirring is continued at room temperature for 1 hr 30 min, and the solution is then poured into 60 ml of methanol and placed in the refrigerator for 12 hours. The precipitate formed is drained and taken up in 10 ml of water and this is poured into 60 ml of methanol. The solution is maintained at 0° C. for 2 hours and the crystals of the monosodium derivative of S-(2-glycylaminoethyl)phosphorothioic acid are drained and dried under vaccum in a desiccator containing phosphoric anhydre(sic). Approximately 1.4 g of very hygroscopic salt is collected.

NMR spectrum (D$_2$O) δ ppm: 3.86 (S-2H) gly. CH$_2$; 3.40 and 2.80 (2m-4H) N—CH$_2$—CH$_2$—S.

*Trisodium phosphorothioate is prepared according to the method of S. AKERFELOT, Acta. Chem. Scand. 1960, 14, 1980-84.

EXAMPLE 45

N,N'-DIALANYLCYSTAMINE DI(TRIFLUOROACETATE)

The reaction is performed as in Examples 17 and 18, replacing glycine by alanine, the molar proportions remaining the same. After lyophilisation, this product takes the form of an oil.

NMR spectrum (D$_{20}$) (sic): 3.98 (m) CH: 3.48 (m) N—CH$_2$; 2.76(t) S—CH$_2$; 1.46 (d), CH$_3$.

EXAMPLE 46

RADIOPROTECTIVE ACTIVITY

This study of radioprotective activity was carried out according to a technique described by M. Fatome at al., Eur. J. Med. Chem. 1977, 12, (1), 93. Substances were injected intraperitoneally at the doses shown in Table I, 15 minutes before irradiation at the LD$_{100}$/30 days level. This dose is equal to 950 Rad.

More complete studies are recorded in Table II.

TABLE I

Survival rate at the 30th day
(injection of the drugs 15' before irradiation at 900 or 950 Rad)

| Compound of Example | LD$_{50}$ (mg/kg) | Doses (mg/kg i.p.) | % survival |
|---|---|---|---|
| 2 | 1,500 | 750 | 100 |
|   |       | 187 | 67 |
| 4 | 1,500 | 750 | 80 |
|   |       | 188 | 40 |
| 6 | 800 | 400 | 60 |
| 8 | 1,200 | 750 | 93 |
| 10 | 800 | 800 | 40 |
| 16 | 1,500 | 750 | 100 |
| 18 | 1,200 | 750 | 100 |
| 19 | 800 | 400 | 100 |
| 45 | 1,200 | 600 | 100 |
| 22 | 1,250 | 625 | 100 |
| 24 | 1,500 | 750 | 70 |
| 26 | 1,200 | 750 | 60 |
| 28 | >2,000 | 1,000 | 100 |
| 31 | 750 | 375 | 60 |
| 32 | 1,500 | 1,000 | 100 |
| 34 | 1,000 | 500 | 70 |
| 36 | 2,000 | 1,000 | 30 |

TABLE II

| Compound of the Example | Formulae | LD$_{50}$ mg/kg (i.p.) | Doses administered mg/kg (i.p.) | Time of administration before irradiation | Radiation doses (Rad) | % survival at 30 days |
|---|---|---|---|---|---|---|
| 8 | TFA, H$_2$N—CH$_2$—CO—NH—CH$_2$—CH$_2$—S—COCH$_3$ | 1,200 | 750 | 15' | 900 | 93 |
|   |   |   | 187 | 15' | 900 | 0 |
|   |   |   | 750 | 15' | 1,100 | 50 |

TABLE II-continued

| Compound of the Example | Formulae | $LD_{50}$ mg/kg (i.p.) | Doses administered mg/kg (i.p.) | Time of administration before irradiation | Radiation doses (Rad) | % survival at 30 days |
|---|---|---|---|---|---|---|
| 18 | TFA, $H_2N-CH_2-CO-NH-CH_2-CH_2-S$<br>                                                                                                                                                                                                                                                               |<br>TFA, $H_2N-CH_2-CO-NH-CH_2-CH_2-S$ | 1,250 | 750<br>187<br>750<br>750<br>1,000<br>750<br>187<br>94<br>47 | 15'<br>15'<br>2 hours<br>15'<br>15'<br>15'<br>15'<br>15'<br>15' | 900<br>900<br>900<br>1,100<br>1,300<br>1,300<br>1,100<br>900<br>900 | 100<br>90<br>60<br>100<br>0<br>10<br>0<br>30<br>0 |
| (sic) | TFA, $H_2N-CH-CO-NH-CH_2-CH_2-S$<br>            |<br>            $CH_3$<br>TFA, $H_2N-CH-CO-NH-CH_2-CH_2-S$<br>            |<br>            $CH_3$ | 1,200 | 600<br>150<br>600<br>600 | 15'<br>15'<br>2 hours<br>15' | 900<br>900<br>900<br>1,100 | 100<br>20<br>50<br>50 |
| 22 | TFA, $H_2N-CH-CO-NH-CH_2-CH_2-S-COCH_3$<br>           |<br>           $CH_3$ | 1,250 | 625<br>625<br>625<br>156 | 15'<br>15'<br>2 hours<br>15' | 900<br>1,100<br>900<br>900 | 100<br>50<br>10<br>0 |
| 24 |                         $CH_3$<br>                        |<br>TFA, $H_2N-CH_2-CO-S-CH_2-C-NH-COCH_3$<br>                        |<br>                        $CH_3$ | 1,500 | 750<br>750<br>750 | 15'<br>2 hours<br>15' | 900<br>900<br>1,100 | 70<br>50<br>13 |
| 26 |                         $CH_3$<br>                        |<br>TFA, $H_2N-CH_2-CO-NH-C-CH_2-S-COCH_3$<br>                        |<br>                        $CH_3$ | 1,200 | 750<br>187<br>750<br>750 | 15'<br>15'<br>2 hours<br>15' | 900<br>900<br>900<br>1,100 | 60<br>40<br>70<br>0 |
| 28 | TFA, $H_2N-CH_2-CO-NH-CH_2-CO-NH(CH_2)_2S-CO$<br>                                                                                                                                                                                                                                                                                                $CH_3$ | >2,000 | 1,000<br>1,000<br>1,500 | 15'<br>15'<br>15' | 900<br>1,100<br>1,100 | 100<br>0<br>100 |
| 31 | TFA, $H_2N-CH_2-CO-NH-CH_2-CH-CH_2-S$<br>                                               $OCOCH_3$<br>TFA, $H_2N-CH_2-CO-NH-CH_2-CH-CH_2-S$<br>                                               $OCOCH_3$ | 750 | 375<br>93.7<br>375 | 15'<br>15'<br>2 hours | 900<br>900<br>900 | 60<br>0<br>0 |
| 32 | TFA, $H_2N-CH_2-CO-NH-CH_2-CH-CH_2-S-CO$<br>                                               $OCOCH_3$    $CH_3$ | 1,500 | 1,000<br>250<br>1,000 | 15'<br>15'<br>15' | 900<br>900<br>1,100 | 100<br>70<br>80 |
| 34 | TFA, $H_2N-CH_2-CO-S-CH_2-CH_2-NH-COCH_3$ | 1,000 | 500<br>125 | 15'<br>15' | 950<br>950 | 70<br>20 |
| 36 | TFA, $H_2N-CH_2-CO-NH-CH_2-CO-NH-CH_2-CH_2-S$<br>                                                                                                                                                                                                                                                                                                                                                |<br>TFA, $H_2N-CH_2-CO-NH-CH_2-CO-NH-CH_2-CH_2-S$ | 2,000 | 1,000<br>250 | 15'<br>15' | 950<br>950 | 30<br>10 |

Several comments can be made regarding these results.

First, the two higher homologues I 106 (Example 22) and I 105 (Example 45) of I 102 (Example 8) and I 103 (Example 18) described exhibit good radioprotection with low toxicity. However, replacement of glycine by L-alanine does not bring about large changes as regards the radioprotective activity, the better amino acid nevertheless remaining glycine.

The derivatives I 107 (Example 24) and I 108 (Example 28) contain a glycine for reasons which have been put forward, and a dimethylated cysteamine in the α-position to the nitrogen atom chosen by analogy with a thiosulphate described by Piper et al.: $H_2N-(C(CH_3)_2-CH_2-S-SO_3H$ (J. R. Piper et al., J. Med. Chem. 1966, 9, 911), which compound exhibits a good protection at 600 mg/kg. These two products, acetylated at the end of the chain, show radioprotective activity; this could be predicted for I 108, but a new development has emerged since I 107 is an S-glycyl instead of an S-acetyl compound, and on this occasion the terminal amine of the cysteamine contains an acetyl group. Since the activity is linked to liberation of the thiol in vivo, there must hence be a libertation of the glycyl group in this case.

The molecule I 109 (Example 28) is especially useful. This is the first molecule to have a dipeptide sequence on S-acetylated cysteamine. By using a dipeptide (gly-gly), it was hoped to reduce the toxicity relative to I 102 while preserving radioprotective activity.

The first results obtained are very encouraging, since the $LD_{50}$ of I 509 is >2,000 mg/kg. Its activity, which requires further study, is quite exceptional since 100% survival at 30 days is observed in mice which have received 1,500 mg/kg (i.p.) of drug 15 minutes before an irradiation of 1,100 Rad.

Compounds I 110 (Example 31) and I 111 (Example 32) were synthesized by analogy with WR 77913 ($H_2N-CH_2-CH(OH)-CH_2-S-PO_3HNa$) which gives 100% survival at 30 days in mice which have received 400 mg/kg (i.p.) 30 minutes before an irradiation of 950; 970 Rad (J. R. Piper et al., J. Med. Chem. 1975, 18, 804).

The results are still partial; nevertheless, I 111, which is of low toxicity ($LD_{50}$>1,500) shows 80% survival at 30 days at 1,000 mg/kg (1,100 Rad) and 70% at 250 mg/kg (900 Rad).

As regards the derivative I 114 (Example 34), this possesses an S-glycyl union (see I 107) and can be considered to be the reverse of I 102, it exhibits a slight radioprotective action.

EXAMPLE 47
ANTI-CARCINOGENIC ACTIVITY

Drug used: HBr, $H_2N-CH_2-(C=O)-NH-(C_2-)_2-S-(C=O)-CH_3$ (I 102)

The anti-carcinogenic activity was determined in mice bearing EMT6 or HT19 tumours. 695 mg/kg are injected i.p. 15 minutes before the start of irradiation at 20 Gy.

In the first case, for a dose of 20 Gy, a survival of $10^{-2}$ is observed, but with administration of the drug the cellular survival is between 5 and $8 \times 10^{-2}$ (according to whether or not the cloning coefficient is taken into account).

For the second type of tumour, a survival of $10^{-2}$ is observed for a dose of 20 Gy, but with administration of the drug the cellular survival is between 2.4 and $4 \times 10^{-2}$ (same comment).

It is hence observed that this compound, in addition to its radioprotective power, does not protect tumours (or protects them to only a small extent), except if the latter are necrotised.

One of the best current radioprotectors, WR 2721, is structurally close to I 102 since it contains a cysteamine united to a propylamine group, and has its thiol group protected by a phosphorothioate group (unstable moreover, leading to the problems encountered in purifying WR 2721). Furthermore, it was shown, principally by the work of Yuhas, that WR 2721 possessed the exceptional property of concentrating selectively in normal tissues (and not in cancer cells).

In consequence, it selectively protects normal tissues against radiation-induced damage, while allowing solid tumours to bear alone the effect of radiation.

Now, since the number of cancers induced by radiotherapy is not insignificant, this would be a drug of choice which could be used very generally during all treatments of cancer by this approach.

Moreover, it would also appear that WR 2721 can exert a selective protective effect during chemotherapy performed with alkylating drugs.

It has recently been shown that the model compound I 102 possessed this same selectivity.

Although the starting model compound (I 102) possesses a lower FRD than WR 2721 (respectively, 1.4 and 2.7 on bone marrow), the gain factor (bone marrow FRD/tumour FRD) for a $5 \times 10^{-1}$ survival level on EMT 6 tumours is identical for the two products, and equal to 1.2.

Furthermore, I 102 shows two advantages compared with WR 2721:
greater chemical stability (WR 2721 is, in fact, not very stable, and this sometimes leads to non-reproducible results),
lower toxicity ($LD_{50}$ >1,500 mg/kg and 950 mg/kg, respectively).

ABBREVIATIONS USED IN THE EXPERIMENTAL SECTION

Z: benzyloxycarbonyl
t-PNC: hexachlorocyclotriphosphazene
THF: tetrahydrofuran
TEA: triethylamine
TLC: thin layer chromatography (Merck 605 254 silica gel)
BOC: tert-butoxycarbonyl
AA: amino acid or a radical corresponding to $R_1-CO-$
TFA: trifluoroacetic acid
AcOEt: ethyl acetate
NMR spectrum: s=singlet, d=doublet, t=triplet, m=multiplet
Commercial products obtained from Fluka
MEA: β-mercaptoethylamine (cysteamine)
φ: temperature
DMF: dimethylformamide
MEA: $NH_2-CH_2-CH_2-SH$ or the corresponding radical
Column chromatography carried.out with Merck 60 silica gel (70-230 mesh)

We claim:

1. Compound of formula I:

in which
$R_1-CO-$ is an amino acid residue wherein $R_1$ is a linear or branched $C_{1-7}$ alkylamino radical,
/A/ is a $C_2$ or $C_3$ alkylene moiety which can be substituted with a $C_1$ to $C_3$ alkyl radical, a hydroxy or hydroxycarbonyl radical, or a -COR radical where R is an amino or $-NH-CH_2-CO_2H$ radical,
$R_2$ is the radical

where $R_4$ is oxygen and $R_5$=H, $C_1$-$C_7$ alkyl, phenyl or phenyl substituted with one or more halogen atoms, $C_1$-$C_3$ alkyl or hydroxy radicals, and
$R_3$ is hydrogen or pharmacologically acceptable acid salts thereof.

2. Compound according to claim 1, in the form of a quaternary ammonium salt, the anion being chosen from: $Br^-$, $Cl^-$, $CF_3CO_2^-$, $CH_3-C_6H_4-SO_3^-$, $CH_3CO_2^-$.

3. Compound according to claim 1 of formula:

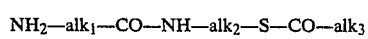

in which $alk_1$ is a linear branched $C_1$ to $C_7$ alkylene chain, $alk_2$ is an ethylenyl or propylenyl chain bearing one or more methyl or hydroxy radicals, and $alk_3$ is a $C_1$–$C_7$-alkyl radical substituted with one or more chlorine atoms.

4. Compound according to claim 1, N-glycyl-S-acetylcysteamine or a pharmacologically acceptable salt thereof.

5. Compound according to claim 1, N-L-alanyl-S-acetylcysteamine or a pharmacologically acceptable salt thereof.

6. Compound according to claim 1, N-γ-aminobutyryl-S-acetylcysteamine or a pharmacologically acceptable salt thereof.

7. Compound according to claim 1, N-glycyl-S-(dichloroacetyl)cysteamine or a pharmacologically acceptable salt thereof.

8. Compound according to claim 1 of formula:

$$NH_2—alk_1—CO—NH—alk_2—S—CO—alk_3$$

in which $alk_1$ is a linear or branched $C_1$ to $C_7$ alkylene chain, $alk_2$ is an ethylenyl or propylenyl chain bearing one or more methyl or hydroxy radical, and $alk_3$ is a $C_1$–$C_7$-alkyl radical either unsubstituted or substituted with one or more chlorine atoms.

9. A pharmaceutical composition effective in the protection of normal tissues against radiation induced damage comprising a protective amount of a compound of claim 1 effective to afford such protection upon intraperitoneal administration.

10. A method of protecting normal tissues against radiation induced damage comprising
intraperitoneally administering an effective dose of a compound of formula I as defined in claim 1.

* * * * *

UNITED STATES PATENT AND TRADEMARK OFFICE
CERTIFICATE OF CORRECTION

PATENT NO. : 4,816,482

DATED : March 28, 1989

INVENTOR(S) : Joel OIRY et al

It is certified that error appears in the above-identified patent and that said Letters Patent is hereby corrected as shown below:

On cover page, Item [63], please change

"20" to -- 21 --.

Signed and Sealed this

Sixth Day of March, 1990

*Attest:*

JEFFREY M. SAMUELS

*Attesting Officer*        *Acting Commissioner of Patents and Trademarks*